United States Patent
Pace-Asciak et al.

(10) Patent No.: US 8,710,252 B2
(45) Date of Patent: Apr. 29, 2014

(54) HEPODXILIN ANALOG ENANTIOMERS

(75) Inventors: Cecil Pace-Asciak, Toronto (CA);
 Alexandra SantAna Sorensen,
 Allschwil (CH); Jean-Philippe Meyer,
 Strasbourg (FR); Peter Denim, Moscow
 (RU)

(73) Assignee: Cecil Pace-Asciak, Toronto (CA)

( * ) Notice: Subject to any disclaimer, the term of this patent is extended or adjusted under 35 U.S.C. 154(b) by 951 days.

(21) Appl. No.: 12/226,457

(22) PCT Filed: Apr. 19, 2007

(86) PCT No.: PCT/CA2007/000668
§ 371 (c)(1),
(2), (4) Date: Apr. 20, 2010

(87) PCT Pub. No.: WO2007/118335
PCT Pub. Date: Oct. 25, 2007

(65) Prior Publication Data

US 2010/0210727 A1 Aug. 19, 2010

Related U.S. Application Data

(60) Provisional application No. 60/844,356, filed on Sep. 14, 2006, provisional application No. 60/833,477, filed on Jul. 27, 2006, provisional application No. 60/794,584, filed on Apr. 25, 2006, provisional application No. 60/793,008, filed on Apr. 19, 2006.

(51) Int. Cl.
*C07C 57/00* (2006.01)
*C07C 59/11* (2006.01)
*A61K 31/20* (2006.01)
*C07C 69/74* (2006.01)

(52) U.S. Cl.
USPC .......... 554/221; 554/214; 554/215; 554/148; 514/559; 514/560; 514/738; 560/124

(58) Field of Classification Search
None
See application file for complete search history.

(56) References Cited

U.S. PATENT DOCUMENTS

| | | |
|---|---|---|
| 5,616,607 A | 4/1997 | Pace-Asciak et al. |
| 5,783,564 A | 7/1998 | Chaki et al. ............ 514/42 |

(Continued)

FOREIGN PATENT DOCUMENTS

| | | |
|---|---|---|
| CA | 2159584 | 10/1994 |
| WO | WO 94/22848 | 10/1994 |

(Continued)

OTHER PUBLICATIONS

Darrow, J., The patentability of Enantiomers: Implications for the pharmaceutical industry, 2007, Stanford Technology Law Review, 19 pages.*

(Continued)

*Primary Examiner* — Yate K Cutliff

(57) ABSTRACT

The present invention relates to enantiomeric forms of hepoxilin analogs of Formula I-VIII, pharmaceutical compositions thereof, a method for the separation of said enantiomeric forms of hepoxilin analogs comprising applying said hepoxilin to a chiral phase HPLC column and eluting said hepoxilin with an alkane and alcohol solvent mixture. Said enantiomeric forms of hepoxilin analogs of Formula I-VIII were found to be useful in controlling the biological effects of PPAR mediated transcriptional control for the treatment of diseases such as cancer, thromboxane-mediated diseases and for modulating intracellular calcium concentration.

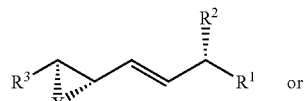

I

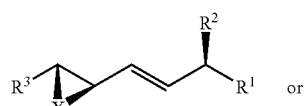

II

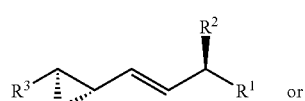

III

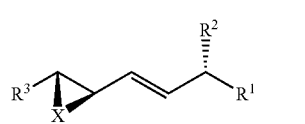

IV

19 Claims, 7 Drawing Sheets

(56) References Cited

U.S. PATENT DOCUMENTS

| | | | |
|---|---|---|---|
| 6,093,741 | A | 7/2000 | Gosselin et al. |
| 6,391,305 | B1 | 5/2002 | Feng et al. |
| 6,673,785 | B1 | 1/2004 | Pace-Asciak ................ 514/183 |

FOREIGN PATENT DOCUMENTS

| | | | |
|---|---|---|---|
| WO | WO 97/29751 | | 8/1997 |
| WO | WO 99/59578 | | 11/1999 |
| WO | WO 00/07589 | | 2/2000 |
| WO | WO 01/10422 | | 2/2001 |
| WO | WO 0134551 | * | 5/2001 |
| WO | WO 02/38157 | | 5/2002 |
| WO | WO 03/099285 | | 12/2003 |

OTHER PUBLICATIONS

Henke, B.R., Peroxisome Proliferator-activated receptero alpha/gamma dual agonist for the treatment of type 2 diabetes, 2004, J. Med. Chem, vol. 47, 4118-4127.*

Alali, Feras Q. et al., 2,4-Cis and Trans)-Gigantecinone and 4-Deoxygigantecin, Bioactive Nonadjacent Bis-Tetrahydrofuran Annonaceous Acetogenins, from Goniothalamus Giganteus, J. Nat. Prod., (1997), vol. 60, pp. 929-933.

Antón, R. et al., Occurrence of Hepoxilins and Trioxilins in Psoriatic Lesions, J. Investigative Dermatology, Inc., (1998), vol. 110, pp. 303-310.

Arndt, et al., Liposomal Bleomycin: Increased Therapeutic Activity and Deceased Pulmonary Toxicity in Mice Drug Delivery, (2001), vol. 8, pp. 1-7.

Chawla, Ajay et al., Peroxisome Proliferator and Retinoid Signaling Pathways Co-Regulate Preadipocyte Phenotype and Survival, Proc. Natl. Acad. Sci. USA, (1994), vol. 91, pp. 1786-1790.

Chen J. Don et al., A Transcriptional Co-Repressor that Interacts with Nuclear Hormone Receptors, Letters to Nature, (1995), vol. 377, pp. 454-457.

Cheng, G.S., Dramatic Results in Trial of New Leukemia Drug, Family Practice News, (2000), p. 1.

Corey, E. J. et al., Total Synthesis of 12-(S)-Hydroxy-Trans-11,12-Epoxyeicosa-5,9,14-(Z)-Trienoic Acids, Metabolites of Arachidonic Acid in Mammalian Blood Platelets, Tetrahedron Letters, (1983), vol. 25, No. 45, pp. 4914-4916.

Demin, Peter et al., High-Performance Liquid Chromatographic Separation of Fluorescent Esters of Hepoxilin Enantiomers on a Chiral Stationary Phase, J. Chromatogr. B, (1995), vol. 672, pp. 282-289.

Demin, P. M. et al., Chem. Abstracts 113: 40257x, (1990).

Demin, P.M. et al., Chem. Abstracts 114: 42306g, (1991).

Demin, P. M. et al., Synthesis of Racemic 11,12-Cyclopropyl Analogs of Hepoxilins $A_3$ and $B_3$, Tetrahedron Letters, (1993), vol. 34, pp. 4305-4308.

Dias, Nathalie et al., Antisense Oligonucleotides: Basic Concepts and Mechanisms, Molecular Cancer Therapeutics, (2002), vol. 1, pp. 347-355.

Fernandes, R. A. et al., Asymmetric Dihydroxylation and One-Pot Epoxidation Routes to (+)- and (−)-Posticlure: A Novel Trans-Epoxide as a Sex Pheromone Component of Orgyia Postica (Walker), Tetraherdron, (2002), vol. 58, pp. 6685-6690.

Goodman & Gilman's: The Pharmacological Basis of Therapeutics, 10th Edition, McGraw-Hill Medical Publishing Division (2001,) pp. 54-57.

Grinstein, S. et al., Amiloride-Sensitve Na+/H+ Exchange in Human Neutrophils: Mechanism of Activation by Chemotactic Factors, BBRC, (1984), vol. 122, pp. 755-762.

Hallett, M. B. et al., Direct Measurement of Intracellular Free $Ca^{2+}$ in Rat Peritoneal Macrophages: Correlation with Oxygen-Radical Production, Immunology, (1983), vol. 50, pp. 487-495.

Helledie, Torben et al., Lipid-Binding Proteins Modulate Ligan-Dependent Trans-Activation by Peroxisome Proliferator-Activated Receptors and Localize to the Nucleus as well as the Cytoplasm, J. Lipid Res., (2000), vol. 41, pp. 1740-1751.

Jaconi, M. E. E. et al., The Regulation of Store-Dependent $Ca^{2+}$ Influx in HL-60 Granulocytes Involves GTP-Sensitive Elements, J. Biol. Chem., (1993), vol. 268, pp. 26075-26078.

Jankov, Robert P. et al., Hepoxilin Analogs Inhibit Bleomycin-Induced Pulmonary Fibrosis in the Mouse, J. Pharm. Exp. Ther., (2002), vol. 301, pp. 435-440.

Kliewer, S. A. et al., A Prostaglandin $J_2$ Metabolite Binds Peroxisome Proliferator-Activated Receptor γ and Promotes Adipocyte Differentiation, Cell, (1995), vol. 83, pp. 813-819.

Kopelovich, L. et al., Peroxisome Proliferator-Activated Receptor Modulators As Potential Chemoprevetive Agents, Molecular Cancer Therapeutics, (2002), vol. 1, pp. 357-363.

Laneuville, O. et al., Hepoxilin $A_3$ Increases Vascular Permeability in the Rat Skin, Eicosanoids, (1991), vol. 4, pp. 95-97.

Laneuville, O. et al., Hepoxilin $A_3$ Inhibits the Rise in Free Intracellular Calcium Evoked by Formyl-Methionyl-Leucyl-Phenylalanine, Platelet Activating Factor and Leukotriene $B_4$. Biochem. J., (1993), vol. 295, pp. 393-397.

Lapitskaya, M. A. et al., A Chemoselective Synthesis of Functionalized 1,4-Alkadiynes (Skipped Diacetylenes), Synthesis, (1993), pp. 65-66.

Lehmann, J. M. et al., An Antidiabetic Thiazolidinedione is a High Affinity Ligand for Peroxisome Proliferator-Activated Receptor γ (PPARγ), J. Biol. Chem., (1995), vol. 270, pp. 12953-12956.

Li, Xiang et al., The Hepoxilin Analog, PBT-3, Inhibits Growth of K-562 CML Solid Tumors In Vivo in Nude Mice, In Vivo, (2005), vol. 19, pp. 85-190.

Lim, Davin et al., Imatinib for Chronic Myelogenous Leukemia: a NICE Mess, Lancet, (2001), v. 358, p. 1903.

Lozzio, C. B. et al., Human Chronic Myelogenous Leukemia Cell-Line With Positive Philadelphia Chromosome, Blood, (1975), vol. 45 pp. 321-334.

Majumdar, S. et al., Catalytic Asymmetric and Stereoselective Synthesis of Vinylcyclopropanes, Synlett, (2002), No. 3, pp. 423-426.

Martin, S. J. et al., Induction of Apoptosis (Programmed Cell Death) in Human Leukemic HL-60 Cells by Inhibitors of RNA or Protein Synthesis, J. Immunol., (1990), vol. 145, pp. 1859-1867.

Mauro, M. et al., STI571: A Paradigm of New Agents for Cancer Therapeutics. J. Clin. Oncol., (2002), vol. 20, pp. 325-334.

McWhirter, J. R. et al., Activation of Tyrosine Kinase and Microfilament-Binding Functions of c-abl by bcr Sequences in bcr/abl Fusion Proteins, Mol. Cell Biol., (1991), vol. 11, pp. 1553-1565.

Merck Manual Diagnostics, 17th Edition, (1999), pp. 973-995.

Moghaddam, M. F. et al., Discovery of the Mammalian Insulin Release Modulator, Hepoxilin $B_3$, from the Tropical Red Algae Platysiphonia Miniata and Cottoniela Filamentosa, J. Biol. Chem., (1990), vol. 265, pp. 6126-6130.

O'Brien, S.G., Imatinib for Chronic Myelogenous Leukemia: a NICE Mess, Lancet, (2001), pp. 1902-1903.

Omar, M. et al., Asymmetric Sharpless Epoxidation of 13S-Hydroxy-9Z,11E-Octadecadienoic Acid (13S-HODE), Eur. J. Lipid Sci. Technol., (2003), vol. 105, pp. 43-44.

Pace-Asciak, C. R. et al., Hepoxilin Analogs, Potential New Therapeutics in Disease, Current Pharmaceutical Design, (2006), vol. 12, pp. 963-969.

Pace-Asciak, C. R. et al., A New Family of Thromboxane Receptor Antagonists with Secondary Thromboxane Synthase Inhibition, J. Pharmacol. Exper. Ther., (2002), vol. 301, pp. 618-624.

Pace-Asciak, C. R., Chem. Abstracts 105: 58399q, (1986).

Pace-Asciak, C. R. et al., Hepoxilins Modulate Second Messenger Systems in the Human Neutrophil, Cell-Cell Interactions in the Release of Inflammatory Mediators, (1991), pp. 133-139.

Pace-Asciak, C. R. et al., A Glutathione Conjugate of Hepoxilin $A_3$: Formation and Action in the Rat Central Nervous System, Proc. Natl. Acad. Sci USA, (1990), vol. 87, pp. 3037-3041.

Pace-Asciak, C. R., Hepoxilins, Gen Pharma., (1993), vol. 24, pp. 805-810.

Pace-Asciak, C. R. et al., Hepoxilins Raise Circulating Insulin Levels in vivo, FEBS Letters, (1999), vol. 461, pp. 165-168.

Pace-Asciak, C. R. et al., Isolation and Structure of Two Hydroxy Epoxide Intermediates in the Formation of 8,11,12- and 10,11,12-Trihydroxyeicosatrienoic Acids, J. Biol. Chem., (1983), vol. 258, pp. 6835-6840.

(56) References Cited

OTHER PUBLICATIONS

Pace-Asciak, C. R. et al., Resolution by DEAE-Cellulose Chromatography of the Enzymatic Steps in the Transformation of Arachidonic Acid into 8,11,12- and 10,11,12-Trihydroxy-Eicosatrienoic Acid by the Rat Lung, Prostaglandins, (1983), vol. 25, pp. 79-84.

Pace-Asciak, C. R. et al., Oxygenation of Arachidonic Acid into 8,11,12- and 10,11,12-Trihydroxyeicosatrienoic Acid by Rat Lung, Advances in Prostaglandin, Thromboxane, and Leukotriene Research, (1983), vol. 11, pp. 133-139.

Pace-Asciak, C. R., Demonstration Through [$^{18}$O] Oxygen Studies of an Intramolecular Transfer of the Terminal Hydroxyl Group of (12S)-Hydroperoxyeicosa-5,8,10,14-Tetraenoic Acid to Form Hydroxyepoxides, J. Biol. Chem., (1984), vol. 259, pp. 8332-8337.

Pace-Asciak, C. R., Hemoglobin- and Hemin-Catalyzed Transformation of $12_L$-Hydroperoxy-5,8,10,14-Eicosatetraenoic Acid, Biochimica et Biophysica Acta, (1984), vol. 793, pp. 485-488.

Pace-Asciak, C. R. et al., Hepoxilin, A New Family of Insulin Secretagogues Formed by Intact Rat Pancreatic Islets[1], Prostaglandins Leukotrienes and Medicine, (1984), vol. 16, pp. 173-180.

Pace-Asciak, C. R. et al., Hepoxilins, Potential Endogenous Mediators of Insulin Release, Prog. Lipid Res., (1986), vol. 25, pp. 625-628.

Pace-Asciak, C.R. et al., The Hepoxilins, A Review, Lipoxygenases and Their Metabolites, (1999), vol. 447, pp. 123-132.

Prost, I. et al., Evaluation of the Antimicrobial Activities of Plant Oxylipins Supports Their Involvement in Defense Against Pathogens[1][W], Plant Physiology, (2005), vol. 139, pp. 1902-1913.

Qiao, N. et al., The Hepoxilin Analog PBT-3 Induces Apoptosis in BCR-ABL-Positive K562 Leukemia Cells, Anticancer Res., (2003), vol. 23, pp. 3617-3622.

Queiroz, E. F. et al., Determination of the Absolute Configuration of 6-Alkylated α-Pyrones from Ravensara Crassifolia by LC-NMR, Phytochem. Anal., (2003), vol. 14, pp. 34-39.

Rajaratnam, G. et al., Imatinib. for Chronic Myelogenous Leukemia: a NICE Mess, Lancet, (2001), vol. 358, p. 1902.

Rumi, M. A. K. et al., Can PPARγ Ligands Be Used in Cancer Therapy?, Curr. Med. Chem. Anti-Canc. Agents, (2004), vol. 4, pp. 465-477.

Sawyers, C. L., Cancer Treatment in the STI571 Era: What Will Change?, J. Clin Onco, (2001), vol. 19, pp. 13s-16s.

Seppa, N., Leukemia Overpowers Drug in Two Ways, Science News, (2001), vol. 159, p. 389.

Shimizu T. et al., Arachidonic Acid Cascade and Signal Transduction, J. Neurochem, (1990), vol. 55, pp. 1-15.

Spiegelman, B. M., PPAR-γ: Adipogenic Regulator and Thiazolidinedione Receptor, Diabetes, (1998), vol. 47, pp. 507-514.

Sun Lumin, J. R. et al., Palladium Mediated Allylic Mitsunobu Displacement: Stereocontrolled Sythesis of Hepoxilin $A_3$ and Trioxilin $A_3$ Methyl Esters, Tetrahed. Letters, (1992), vol. 33, pp. 2091-2094.

Tan, N. et al. Peroxisome Proliferator-Activated Receptor (PPAR)-β as a Target for Wound Healing Drugs, Am. J. Clin. Dermatol., (2003), vol. 4, pp. 523-530.

Tontonz, P. et al., mPPAR gamma2: Tissue-Specific Regulator of an Adipocyte Enchancer, Genes & Dev., (1994), vol. 8, pp. 1224-1234.

Wang, M. M. et al., Stereoselective Actions of Hepoxilins $A_3$ and $B_3$ and their Cyclopropane Analogs (HXΔ$A_3$ and HXΔ$B_3$) on Bradykinin and PAF-Evoked Potentiation of Vascular Leakage in Rat Skin, Gen. Pharma., (1999), vol. 33, pp. 377-382.

Weisberg, E. et al., Mechanism of Resistance to the ABL Tyrosine Kinase Inhibitor STI571 in BCR/ABL-Transformed Hematopoietic Cell Lines, Blood, (2000), vol. 95, pp. 3498-3505.

International Search Report issued in counterpart International Patent Application No. PCT/CA2007/000668.

Demin, Peter et al., Chemical Synthesis and Actions of 11,12-Thiirano-Hepoxilin $A_3$, J. Lipid Mediators Cell Signalling, (1996), vol. 13, pp. 63-72.

Belardetti, F. et al., Up-and Down-Modulation of Single K$^+$ Channel Function by Distinct Second Messengers, TINS, (1988), vol. 11, pp. 232-238.

Belardetti, F. et al., Products of Heme-Catalyzed Transformation of the Arachidonate Derivative 12-HPETE Open S-Type K$^+$ Channels in Aplysia, Neuron, (1989), vol. 3, pp. 497-505.

Brüne, B. et al., Different Calcium Pools in Humans Platelets and their Role in Thromboxane $A_2$ Formation, Journal of Biological Chemistry, (1991), vol. 266, No. 29, pp. 19232-19237.

Coleman, R. A. et al., Comparison of the Actions of U-46619, A Prostaglandin $H_2$-Analogue, with those of Prostaglandin $H_2$ and Thromboxane $A_2$ on Some Isolated Smooth Muscle Preparations, Br. J. Pharmacol., (1981), vol. 73, pp. 773-778.

Demin, P., et al., Extractive Derivatization of the 12-Lipoxygenase Products, Hepoxilins, and Related Compounds into Fluorescent Anthryl Estes for their Complete High-Performance Liquid Chromatography Profiling in Biological Systems, *Anal. Biochem.* (1995), vol. 226, pp. 252-255.

Dho, S. et al., Hepoxilin $A_3$ Induces Changes in Cytosolic Calcium, Intracellular pH and Membrane Potential in Human, Neutrophils, Biochem. J., (1990), vol. 266, pp. 63-68.

Diczfalusy, U. et al., Enzymatic Conversion of $C_{21}$ Endoperoxides to Thromboxanes and Hydroxy Acids, Biochem. Biophys. Res. Commun., (1980), vol. 94, pp. 1417-1423.

Everts, B. et al., COX-2-Specific Inhibitors—the Emergence of a New Class of Analgesic and Anti-inflammatory Drugs, Clin. Rheumatol., (2000), vol. 19, pp. 331-343.

Fang, X. et al., Functional Implications of a Newly Characterized Pathway of 11,12-Epoxyeicosatrienoic Acid Metabolism in Arterial Smooth Muscle, Circulation Research, (1996), vol. 79, pp. 784-793.

Fiedler, V. B. et al. Reduction of in vivo Coronary Artery Thrombosis by the Novel Thromboxane Antagonist (3R)-3-(4-Fluorophenylsulfonamido)-1,2,3,4-Tetrandro-9-Carbozolepropanoic Acid, Arzneimittelforschung, (1989), vol. 39, pp. 1527-1530.

Fink, M. P., Therapeutic Options Directed Against Platelet Activating Factor, Eicosanoids and Bradykininin Sepsis, Journal of Antimicrobial Chemotherapy, (1998), vol. 41, pp. 81-94.

Fitzgerald, D. J. et al., Thromboxane $A_2$ Synthesis in Pregnancy-Induced Hypertension, Lancet, (1990), vol. 335, pp. 751-754.

Fu, Z .Z. et al., Thromboxane/Prostacyclin Balance in Type II Diabetes: Gliclazide Effects, Metabolism, (1992), vol. 41, pp. 33-35.

Gilutz, H., Deactivation Mechanism of Platelets, Endothelium, (1997), vol. 5, pp. 137-138.

Gorman, R. R. et al., Inhibition of Human Platelet Thromboxane Synthetase by 9,11-Azoprosta-5,13-dienoic Acid, *Proc. Natl. Acad. Sci. USA*, (1977), vol. 74, pp. 4007-4011.

Hamberg, M. et al., Thromboxanes: A New Group of Biologically Active Compounds Derived from Prostaglandin Endoperoxides, Proc. Natl. Acad. Sci. USA, (1975), vol. 72, pp. 2994-2998.

Hamberg, M. et al., Prostaglandin Endoperoxides. Novel Transformations of Arachidonic Acid in Human Platelets, Proc. Nat. Acad. Sci. USA, (1974), vol. 71, pp. 3400-3404.

Hammarstrom, S. et al., Biosynthesis of Thromboxanes, Advances in Prostaglandin and Thromboxane, Research, (1998), vol. 6, pp. 267-274.

Heidemann, S. M. et al., Protective Effects of a Thromboxane Synthetase Inhibitor and Continuous Arteriovenous Hemofiltration in Rat Endotoxic Shock, Prostagl. Leuk. Essen. Fatty Acids, (1997), vol. 56, pp. 473-478.

Hendra, T. et al., Platelet Function, Platelet Prostanoids and Vascular Prostacyclin in Diabetes Mellitus, Prostagl. Leuk. Essen. Fatty Acids., (1989), vol. 35, pp. 197-212.

Himmelstein, S. I., et al., The Role of Thromboxane in Two-Kidney, One-Clip Goldblatt Hypertension in Rats, Am. J. Physiol., (1989), vol. 257, pp. 190-196.

Hishinuma, T. et al., Troglitazone has a Reducing Effect on Thromboxane Production, Prostaglandins & other Lipid Mediators, (2000), vol. 62, pp. 135-143.

Kamijo, T. et al., An Improved and Convenient Procedure for the Synthesis of 1-Substituted Imidazoles, Chem. Pharm. Bull., (1993), vol. 31, pp. 1213-1221.

Laneuville, O. et al., Hepoxilins Sensitize Blood Vessels to Noradrenaline-Stereospecificity of Action, Br. J. Pharmacol., (1992), vol. 105, pp. 297-304.

(56) References Cited

OTHER PUBLICATIONS

Lüscher, T. F. Imbalance of Endothelium-Derived Relaxing and Contracting Factors, Am. J. Hypertens., (1990), vol. 3, pp. 317-330.
Margalit, A. et al., Endogenous Hepoxilin $A_3$, Produced Under Short Duration of High Shear-Stress, Inhibits Thrombin-Induced Aggregation in Human Platelets, Biochim. Biophys. Acta, (1994), vol. 1190, pp. 173-176.
Margalit, A. et al., Low Regulatory Volume Decrease Rate in Platelets from Ischemic Patients: A Possible Role for Hepoxilin $A_3$ in Thrombogenicity, Platelets (Edinburg), Churchill Livingstone Medical Journals, GB, (1995), vol. 6, pp. 371-376.
Margalit, A. et al., Hepoxilin $A_3$ is the Endogenous Lipid Mediator Opposing Hypotonic Swelling of Intact Human Platelets, Proc. Natl. Acad. Sci. (USA), (1993), vol. 90, pp. 2589-2592.
Minuz, P. et al., Prostacyclin and Thromboxane Biosynthesis in Mild Essential Hypertension, Hypertension, (1990), vol. 15, pp. 469-474.
Mitchell, A. et al., Cyclo-Oxygenase-2: Pharmacology, Physiology, Biochemistry and Relevance to NSAID Therapy, British Journal of Pharmacology, (1999), vol. 128, pp. 1121-1132.
Pace-Asciak, C. R., Hepoxilins: A Review on their Cellular Actions, Biochim Biophys. Acta, (1994), vol. 1215, pp. 1-8.
Pace-Asciak, C. R. et al., Hepoxilins: A Review on their Enzymatic Formation, Metobolism and Chemical Synthesis, Lipids, (1995), vol. 30, pp. 107-114.
Pace-Asciak, C. R. et al., Hepoxilin Analogs Inhibit Bleomycin-Induced Pulmonary Fibrosis in the Mouse, J. Pharmacology and Experimental Therapeutics, (2002), vol. 301, pp. 435-440.
Pace-Asciak, C. R. et al., Adv. Prostagl. and Leuk. Res., $11^{th}$. International Conference, Florence, Italy, (2000), Jun. 4-8, Abstr.pp. 18.
Pace-Asciak, C. R., et al., The Red Wine Phenolics Trans-Resveratrol and Quercetin Block Human Platelet Aggregation and Eicosanoid Syntesis: Implications for Protection Against Coronary Heart Disease, Clin. Chim. Acta (1995), vol. 235, pp. 207-219.
Pace-Asciak, C. R. et al., Epoxide Hydratase Assay in Human Platelets using Heposilin $A_3$ as a Lipid Substrate, Biochim. Biophys. Acta, (1986), vol. 875, pp. 406-409.
Parellada, P. P. et al., Action of Selective Inhibitor of Thromboxane Synthetase on Experimental Thrombosis Induced by Arachidonic Acid in Rabbits, Lancet, (1977), p. 40.
Pollock, W. K. et al., Thromboxane-Induced Phosphatidate Formation in Human Platelets, Biochem., J. (1984), vol. 219, pp. 833-842.
Purkerson, M. et al., Inhibitors of Thromboxane Synthesis and Ameliorate the Development of Hypertension in Wistar Rats with Spontaneous Hypertension (SHR), Meeting of the American Society of Nephrology, Washington, D.C. USA, (1985).
Randall, M. J. et al., Acute Arterial Thrombosis in Rabbits: Reduced Platelet Accumulation after Treatment with Thromboxane Synthetase Inhibitor Dazoxiben Hydrochloride, (UK-37, 248-01), Thromb. Res., (1982), vol. 28, pp. 607-616.
Reynaud, D. et al., Hepoxilin $A_3$-Specific Binding in Human Neutrophils, Biochem. J., (1996), vol. 313, pp. 537-541.
Reynaud, D. et al., Novel Platelet Antiaggregating Substances, Biochim. Biophys. Acta., (2001), vol. 3, pp. 580-582.
Reynaud, D. et al., Hepoxilin $A_3$ Formation in the Rat Pineal Gland Selectively Utilizes (12$S$)-Hydroperoxyeicosatetraenoic Acid (HPETE), but not (12$R$)-HPETE, The Journal of Biological Chemistry, (1994), vol. 269, No. 39, pp. 23976-23080.
Silver, R. M. et al., Bacterial Lipopolysaccharide-Mediated Fetal Death, J. Clin. Invest., (1995), vol. 95, pp. 725-731.
Tymkewycz, P. M. et al., Heterogeneity of Thromboxane $A_2$ (TP-)Receptors: Evidence from Antagonist but not Agonist Potency Measurements, Br. J. Pharmacol., (1991), vol. 102, pp. 607-614.
Urban, M., COX-2 Specific Inhibitors Offer Improved Advantages Over Traditional NSAIDs, Orthopedics, (2002), vol. 23, pp. 761-764.
Webster, J. et al., Plasma Levels of 6-Oxo-$PGF_{1\alpha}$, the Hydrolysis Product of Prostacyclin, May be Reduced in Diabetes, Clin. Pharmacol. Prostacyclin, (1981), pp. 113-115.
Wolkow, P. P. et al., Pneumotoxicity of Lipopolysaccharide in Nitric Oxide Deficient Rats is Limited by a Thromboxane Synthase Inhibitor, J. Physiol. Pharmacol., (1997) vol. 48, pp. 645-653.
Yamashita, W. et al., A Thromboxane Synthetase Antagonist has Beneficial Effect on Renal Function in Nephritis with Hypertention, Forty-third Annual National Meeting of the American Federation for Clinical Research Washington, D.C. USA, (1986).
Zaitsu, M. et al., Induction of Cytosolic Phospholipase $A_2$ and Prostaglandin $H_2$ Synthase-2 by Lipopolysaccharide in Human Polymorphonuclear Leukocytes, Eur. J. Haematol., (1999), vol. 63, pp. 94-102.

* cited by examiner

FIGURE 1. Purified enantiomers of PBT-3 racemate showing the structures of the two mirror images Compound A and Compound B.

FIGURE 2. Purified enantiomers of PBT-4 racemate showing the structures of the two mirror images Compound C and Compound D FIGURE 3. Enantiomers of PBT-1 racemate (anti) showing the structures of the two mirror images Compound E and Compound F.

FIGURE 4. Enantiomers of PBT-2 racemate (syn) showing the structures of the two mirror images Compound G and Compound H.

HEPODXILIN ANALOG ENANTIOMERS

This application claims priority under 35 U.S.C. §371 to International Application No. PCT/CA2007/000668, filed Apr. 19, 2007 and entitled "HEPDXILIN ANALOG ENANTIOMERS", which claims priority to U.S. Provisional Patent Application No. 60/844,356, filed Sep. 14, 2006, and U.S. Provisional Patent Application No. 60/833,477, filed Jul. 27, 2006, and U.S. Provisional Patent Application No. 60/794,584, filed Apr. 25, 2006, and U.S. Provisional Patent Application No. 60/793,008, filed Apr. 19, 2006, the contents of each of which are incorporated by reference herein.

FIELD OF THE INVENTION

The invention relates to hepoxilin analogs and more particularly to the separation of enantiomeric forms of hepoxilin analogs and to methods of treatment and pharmaceutical compositions employing the enantiomers.

BACKGROUND OF THE INVENTION

The hepoxilins are biologically active metabolites of arachidonic acid formed through the 12(S)-lipoxygenase pathway. Four natural hepoxilins have been identified, the A-type hepoxilins consisting of two epimers having a hydroxyl group at carbon 8, i.e. 8(S,R)-hydroxy-11(S),12(S)-epoxy-eicosa-5Z,9E,14Z-trienoic acid, and the B-type, two epimers having a hydroxyl group at carbon 10, i.e. 10(S,R)-hydroxy-11(S),12(S)-epoxy-eicosa-5Z,8Z,14Z-trienoic acid.

A number of hepoxilin analogs have been described which exhibit a variety of pharmacological effects, including inhibiting a rise in intracellular calcium (U.S. Pat. No. 5,616,607), reducing inflammation (International Patent Application No. WO 01/010422), inhibiting thromboxane formation and action (International Patent Application No. WO 02/38157), stimulating insulin secretion for the treatment of diabetes (International Patent Application No. WO 01/010422), inhibiting proliferation of neoplastic cells (International Patent Application No. WO 03/099285) and inhibiting the growth of solid tumors (Li et al. (2005); Pace-Asciak et al., (2006)).

The hepoxilins and their analogs contain three asymmetric carbon atoms and can exist in optically active forms or enantiomers, which are mirror images of one another. The prefixes R and S are used to identify the configuration of the molecule about the asymmetric carbons.

The previously described hepoxilin analogs discussed above were produced by processes which result in racemic mixtures of the two enantiomers but resolution of these mixtures into the two distinct enantiomeric forms and characterisation of these enantiomers have not been previously described.

SUMMARY OF THE INVENTION

In an aspect, a new method for the resolution of racemic mixtures of hepoxilin analogs into separated enantiomers is provided.

Native hepoxilins can be resolved into enantiomers by previously described methods (Demin et al., (1995)) but racemic mixtures of the hepoxilin analogs described herein could not be resolved by these methods.

In a further aspect, new enantiomeric forms of hepoxilin analogs with improved biological activity is provided.

In accordance with a further aspect, there is provided a compound of formula:

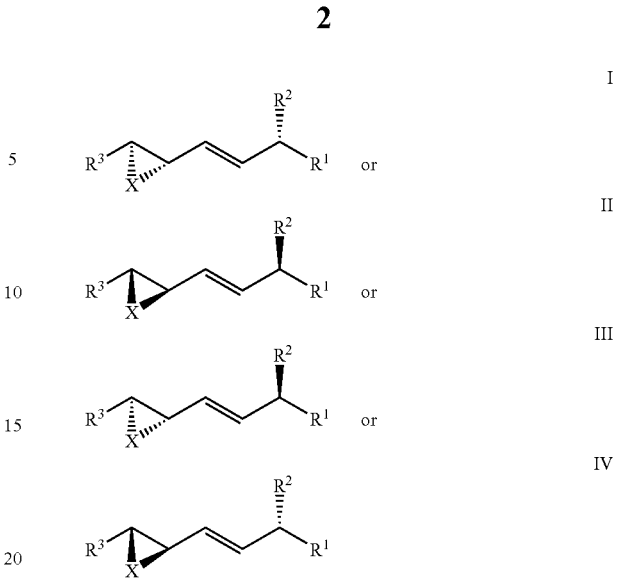

wherein,

X is O, $CH_2$, NH, S, N-alkyl, $(CH_2)_n$ where n is 2, 3 or 4, or $(CH_2)_m$—Y, where Y is S, NH or O and m is 1, 2 or 3;

$R^1$ is lower alkyl, alkenyl or alkynyl; lower alcohol, saturated or unsaturated; aryl; substituted aryl; —$(CH_2)$n-phenyl where n is 1 to 9; or Z—$R^5$, wherein Z is a single bond or a C1-C10 carbon chain optionally substituted with —OH and/or halogen and/or optionally containing up to three double or triple bonds or a mixture of double and triple bonds up to a maximum of three; and $R^5$ is C1-C10 alkyl OH, C1-C10 alkyl-halide, C1-C10 alkyl N3, C1-C10 alkyl —NH2 or $COOR^6$ or $CONHR^6$, and preferably $R^5$ is $COOR^6$ or $CONHR^6$, wherein $R^6$ is H, C5 or C6 cycloalkyl, C5-C6 aryl, a sugar moiety or C1-C10 alkyl or alkenyl optionally substituted with COON, C5-C6 aryl, heterocycle or a sugar moiety, and preferably $R^6$ is $CH_3$, H, alkyl substituted with COOH or a heterocycle;

$R^2$ is H, OH, halogen, $NH_2$, SH, $OPO_3H$, lower alkyl, alkenyl or alkynyl, lower alcohol, O-lower alkyl or alkenyl, S-lower alkyl or alkenyl, NH-lower alkyl or alkenyl, or N bis-lower alkyl or alkenyl; and $R^3$ is a C4-C15 carbon chain optionally substituted with —$OR^7$, wherein $R^7$ is H, lower alkyl, alkenyl or alkynyl; and preferably $R^3$ is an unsubstituted C4 to C10 chain wherein $R^3$ optionally contains up to three double or triple bonds or a mixture of double and triple bonds up to a maximum of three;

or a pharmaceutical salt thereof.

In accordance with another aspect, there is provided a compound of formula:

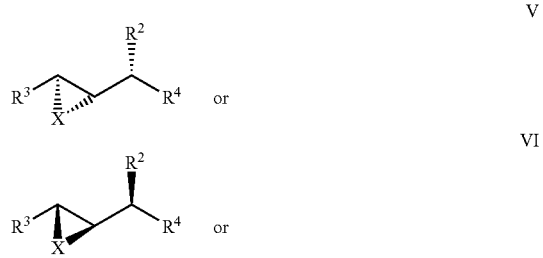

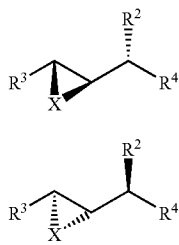

wherein X is O, CH$_2$, NH, S, N-alkyl, (CH$_2$)$_n$ where n is 2, 3 or 4, or (CH$_2$)$_m$—Y, where Y is S, NH or O and m is 1, 2 or 3;

R$^2$ is H, OH, halogen, NH$_2$, SH, OPO$_3$H, lower alkyl, alkenyl or alkynyl, lower alcohol, O-lower alkyl or alkenyl, S-lower alkyl or alkenyl, NH-lower alkyl or alkenyl, or N bis-lower alkyl or alkenyl;

R$^3$ is a C4-C15 carbon chain optionally substituted with —OR$^7$, wherein R$^7$ is —H, lower alkyl, alkenyl or alkynyl; and preferably R$^3$ is an unsubstituted C4 to C10 chain wherein R$^3$ optionally contains up to three double or triple bonds or a mixture of double and triple bonds up to a maximum of three; and R$^4$ is lower alkyl, alkenyl or alkynyl; lower alcohol, saturated or unsaturated; aryl; substituted aryl; —(CH$_2$)$_n$-phenyl where n is 1 to 9; or Z—R$^5$, wherein Z is a single bond or a C1-C10 carbon chain optionally substituted with —OH and/or halogen and/or optionally containing up to three double or triple bonds or a mixture of double and triple bonds up to a maximum of three; and R$^5$ is C1-C10 alkyl OH, C1-C10 alkyl-halide, C1-C10 alkyl N3, C1-C10 alkyl —NH2 or COOR$^6$ or CONHR$^6$, and preferably R$^5$ is COOR$^6$ or CONHR$^6$, wherein R$^6$ is H, C5 or C6 cycloalkyl, C5-C6 aryl, a sugar moiety or C1-C10 alkyl or alkenyl optionally substituted with COOH, C5-C6 aryl, heterocycle or a sugar moiety, and preferably R$^6$ is —CH$_3$, —H, alkyl substituted with COOH or a heterocycle;

or a pharmaceutical salt thereof.

In accordance with a further aspect, the invention provides a compound of the formula I, II, III or IV as defined above, wherein:

X is O, CH$_2$, S or NH;

R$^1$ is COOH, lower alkyl, lower alkenyl, lower alkynyl, aryl, substituted aryl, —(CH$_2$)$_n$-phenyl where n is 1 to 9; lower alkoxy, saturated or unsaturated; —CH$_2$CH═CH—(CH$_2$)$_3$—COR$^8$ wherein R$^8$ is OH, O-lower alkyl or alkenyl; COOR$^6$ or CONHR$^6$, wherein R$^6$ is CH$_3$ or a sugar moiety;

R$^2$ is OH, NH$_2$, SH, OPO$_3$H, lower alkyl or alkenyl; or O-lower alkyl or alkenyl; or N-lower alkyl or alkenyl; or S-lower alkyl or alkenyl; and R$^3$ is lower alkyl, alkenyl or alkynyl; or —CH$_2$—CH═CH—(CH$_2$)$_4$—R$^9$ wherein R$^9$ is CH$_3$, CH$_2$OH, CH$_2$—O-lower alkyl or alkenyl, aryl or substituted aryl, or (CH$_2$)$_n$-phenyl where n is 1 to 9;

or a pharmaceutical salt thereof;

with the proviso that if R$^2$ is OH, and R$^1$ is —CH$_2$CH═CH—(CH$_2$)$_3$—COOH or —CH$_2$CH═CH—(CH$_2$)$_3$—COOCH$_3$ and R$^3$ is —CH$_2$—CH═CH—(CH$_2$)$_4$—CH$_3$, then X is not O.

In accordance with yet a further aspect, there is provided a compound of the formula V, VI, VII or VIII as defined above, wherein:

X is O, CH$_2$, S or NH;

R$^2$ is OH, NH$_2$, SH, OPO$_3$H, lower alkyl or alkenyl; or O-lower alkyl or alkenyl; or N-lower alkyl or alkenyl; or S-lower alkyl or alkenyl;

R$^3$ is lower alkyl, alkenyl or alkynyl; or —CH$_2$—CH═CH—(CH$_2$)$_4$—R$^9$ wherein R$^9$ is CH$_3$, CH$_2$OH, CH$_2$—O-lower alkyl or alkenyl, aryl or substituted aryl, or (CH$_2$)$_n$-phenyl where n is 1 to 9; and R$^4$ is lower alkyl, alkenyl or alkynyl; lower alkoxy, saturated or unsaturated; or —CH═CH —CH$_2$—CH═CH—(CH$_2$)$_3$—COR$^8$ wherein R$^8$ is OH, O-lower alkyl or alkenyl; COOR$^6$ or CONHR$^6$, wherein R$^6$ is CH$_3$ or a sugar moiety;

or a pharmaceutical salt thereof;

with the proviso that if R$^2$ is OH and R$^3$ is —CH$_2$—CH═CH—(CH$_2$)$_4$—CH$_3$ and R$^4$ is —CH═CH—CH$_2$—CH═CH—(CH$_2$)$_3$—COOH or —CH═CH—CH$_2$—CH═CH—(CH2)$_3$—COOCH$_3$, then X is not O.

In an additional aspect, substituted aryl in the above-described formulae is a phenyl substituted with OH, I, Br, Cl or lower alkyl, alkenyl or alkynyl.

In a further aspect, there is provided the following compounds:

(a) 10R-hydroxy-11S,12S-cyclopropyl-eicosa-5Z,8Z,14Z-trienoic acid;
(b) 10R-hydroxy-11R,12R-cyclopropyl-eicosa-5Z,8Z,14Z-trienoic acid;
(c) 8R-hydroxy-11S,12S-cyclopropyl-eicosa-5Z,9E,14Z-trienoic acid;
(d) 10S-hydroxy-11R,12R-cyclopropyl-eicosa-5Z,8Z,14Z-trienoic acid;
(e) 10S-hydroxy-11S,12S-cyclopropyl-eicosa-5Z,8Z,14Z-trienoic acid;
(f) 8S-hydroxy-11R,12R-cyclopropyl-eicosa-5Z,9E,14Z-trienoic acid;
(g) 8S-hydroxy-11S,12S-cyclopropyl-eicosa-5Z,9E,14Z-trienoic acid;
(h) 8R-hydroxy-11R,12R-cyclopropyl-eicosa-5Z,9E,14Z-trienoic acid; and
(i) a pharmaceutical salt thereof, a methyl ester, sugar amide, or sugar ester of any of compounds (a) to (h).

In a further aspect, there is provided the compound 10R-hydroxy-11S,12S-cyclopropyl-eicosa-5Z,8Z,14Z-trienoic acid (Compound A).

In another aspect, there is provided the compound 10S-hydroxy-11R,12R-cyclopropyl-eicosa-5Z,8Z,14Z-trienoic acid (compound B), 10S-hydroxy-11S,12S-cyclopropyl-eicosa-5Z,8Z,14Z-trienoic acid (compound D) 8S-hydroxy-11R,12R-cyclopropyl-eicosa-5Z,9E,14Z-trienoic acid (compound F) or their respective methyl esters or pharmaceutical salt thereof. These enantiomers, and more specifically compound F, are of particular interest for the modulation of the activity of peroxisome proliferation activating receptor (PPAR), such as selective PPAR gamma modulation.

The invention also includes pharmaceutically acceptable salts of all of the above-described compounds when R$^1$ or R$^4$ terminates in COOH. Such pharmaceutically acceptable salts include Na, K, Ca or hemi-Ca, Li, Mg or hemi-Mg, Zn, Al and Fe salts and amine salts such as N-methylglucamine. Pharmaceutically acceptable salts also include acid-addition salts, including salts of organic acids and mineral acids. Examples of such salts include organic acids such as formic acid, acetic acid, propionic acid, glycolic acid, lactic acid, pyruvic acid, oxalic acid, succinic acid, malic acid, tartaric acid, citric acid, benzoic acid, salicylic acid, tris hydroxyl amino methyl (THAM) and the like. Suitable inorganic acid-addition salts include salts of hydrochloric, hydrobromic, sulfuric and phosphoric acids and the like. The acid addition salts may be obtained as the directed products of compound synthesis. In the alternative, the free base may be dissolved in a suitable solvent containing the appropriate acid, and the salt isolated by evaporating the solvent or otherwise separating the salt and solvent.

In still a further aspect, there is provided a pharmaceutical composition comprising at least one of the above-described compounds or pharmaceutically acceptable salts thereof. The pharmaceutical composition may further comprise a pharmaceutically acceptable carrier.

In accordance with a further aspect is a method for treating cancer in a mammal comprising administering to the mammal an effective amount of one or more of the above-described compounds. The cancer may be, for example, leukemia, carcinoma, sarcoma, adenocarcinoma, lymphoma, brain cancer or cancer of the lungs, prostate, breast, bladder or gut.

The above-described compounds may be employed to inhibit platelet aggregation, as thromboxane receptor agonists, as PPAR agonists, to inhibit proliferation of neoplastic cells or to decrease blood glucose levels.

In accordance with a further aspect is a method for treating or preventing a clinical condition such as metabolic syndrome, obesity, insulin resistance, pre-diabetes, diabetes, dyslipidemia, thrombosis, autoimmune disease, such as multiple sclerosis, psoriasis, atopic dermatitis, asthma and ulcerative colitis, ichthyosis, cancer, such as liposarcoma, neuroblastoma, bladder, breast, colon, lung, pancreas and prostate cancers, inflammation, ocular disease, viral infection (including AIDS) and wound healing, comprising administering to the mammal an effective amount of one or more of the above-described compounds or a pharmaceutically acceptable salt thereof.

The compounds described herein may be used in the preparation of a medicament for the treatment or prevention of the above-described clinical conditions.

In another aspect, there is provided a use of the compounds of the invention for the preparation of a medicament for modulating PPAR activity, for example for prevention or treatment of a PPAR-gamma mediated disease or condition, in particular any of the PPAR gamma mediated diseases or conditions described herein.

In accordance with a further aspect, there is provided a method for separating a racemic mixture of a hepoxilin analog into enantiomers comprising:

applying the racemic hepoxilin analog to a chiral phase HPLC column; and eluting the racemic hepoxilin analog with a solvent comprising at least one alkane and at least one alcohol in a ratio of from about 99.9:0.1 to about 90:10 to separate the enantiomers.

BRIEF DESCRIPTION OF THE DRAWINGS

Certain embodiments will now be described more fully with reference to the accompanying drawings.

DETAILED DESCRIPTION OF THE INVENTION

Figure 1:
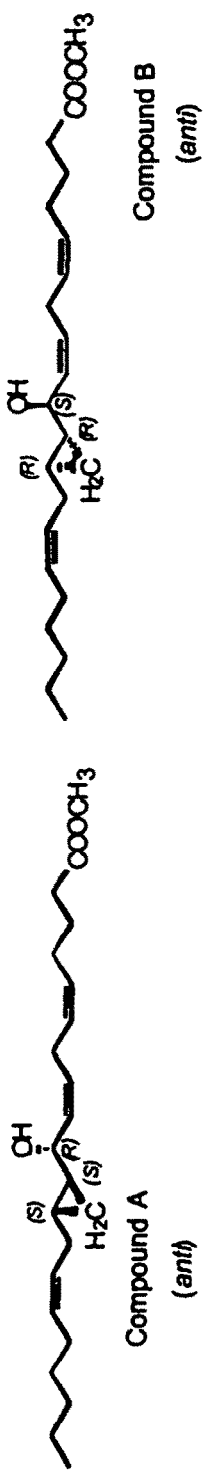
FIG. 1 shows structures of enantiomers of PBT-3.

In general, the terms used herein have the standard definitions that one of ordinary skill in the pharmaceutical, biological and chemical arts would employ in understanding the invention, unless otherwise clear from the context. As used herein, the following definitions are used:

Agonist/Antagonist: Compounds capable of modulating the activity of a receptor can be full agonists, partial agonists/partial antagonists, or full antagonists. By "agonist" is meant a compound or composition which when combined with a receptor stimulates or increases a reaction typical for the receptor, e.g., PPAR-mediated transcription activation activity. Similarly, by "antagonist" is meant a compound or composition which when combined with a receptor reduces a reaction typical for that receptor, e.g., inhibition of platelet aggregation through binding to the thromboxane receptor.

Selective modulation: The term "selective" in reference to modulation, an agonist or antagonist means that a compound preferentially binds to or acts on one or fewer than all receptor sub-types (or iso-types). For example, by selective PPAR modulation, it is meant that the PPAR modulator is not a pan-agonist (i.e., activating PPAR gamma, PPAR delta and PPAR alpha) or antagonist, but acts selectively on one (or two in the case of dual agonists/antagonists) of PPAR gamma, PPAR delta and PPAR alpha, and typically will not bind to other nuclear receptors.

Alkyl: The term "alkyl" refers to a monovalent, saturated aliphatic hydrocarbon radical having the indicated number of carbon atoms, generally one to twenty two. For example, a "C1-C6 alkyl" or an "alkyl of 1-6 carbons" or "Alk 1-6" would refer to any alkyl group containing one to six carbons in the structure. "C1-C22 alkyl" refers to any alkyl group having one to twenty two carbons. "C1-C10 alkyl" would refer to an alkyl of one to ten carbons. Alkyl may be a straight chain (i.e. linear) or a branched chain. Lower alkyl refers to an alkyl of 1-6 carbons. Representative examples of lower alkyl radicals include methyl, ethyl, n-propyl, n-butyl, n-pentyl, n-hexyl, isopropyl, isobutyl, isopentyl, amyl, sec-butyl, tert-butyl, sec-amyl, tert-pentyl, 2-ethylbutyl, 2,3-dimethylbutyl, and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted.

Alkenyl: The term "alkenyl" refers to a monovalent, aliphatic hydrocarbon radical having at least one carbon-carbon double bond and having the indicated number of carbon atoms. For example, a "C2-C6 alkenyl" or an "alkenyl of 2-6 carbons," or "alkenyl 2-6" would refer to an alkenyl group containing two to six carbon atoms in the structure. "C2-C20 alkenyl" refers to any alkenyl group having one to twenty carbons. Alkenyl may be a straight chain (i.e., linear) or a branched chain. Lower alkenyl refers to an alkenyl of 2-6 carbons. Representative examples of lower alkenyl radicals include ethenyl, 1-propenyl, 1-butenyl, 1-pentenyl, 1-hexenyl, isopropenyl, isobutenyl, and the like. Higher alkenyl refers to alkenyls of seven carbons and above. These include 1-heptenyl, 1-octenyl, 1-nonenyl, 1-decenyl, 1-dodecenyl, 1-tetradecenyl, 1-hexadecenyl, 1-octadecenyl, 1-eicosenyl, and the like, along with branched variations thereof. The radical may be optionally substituted.

Alkynyl: The term "alkynyl" refers to a monovalent, aliphatic hydrocarbon radical having at least one carbon-carbon triple bond and having the indicated number of carbon atoms. For example, a "C2-C6 alkynyl" or an "alkynyl of 2-6 carbons," or "alkynyl 2-6" would refer to an alkynyl group containing two to six carbon atoms in the structure. "C2-C20 alkynyl" refers to any alkynyl group having one to twenty carbons. Alkynyl may be a straight chain (i.e., linear) or a branched chain. Lower alkynyl refers to an alkynyl of 2-6 carbons. Representative examples of lower alkynyl radicals include ethynyl, 1-propynyl, 1-butynyl, 1-pentynyl, 1-hexynyl, isopropynyl, isobutynyl, and the like. Higher alkynyl refers to alkynyls of seven carbons and above. These include 1-heptynyl, 1-octynyl, 1-nonynyl, 1-decynyl, 1-dodecynyl, 1-tetradecynyl, 1-hexadecynyl, 1-octadecynyl, 1-eicosynyl, and the like, along with branched variations thereof. The radical may be optionally substituted.

Alkoxy: The term "alkoxy" refers to a monovalent radical of the formula RO—, where R is an alkyl, alkenyl or alkynyl as defined herein. Lower alkoxy refers to an alkoxy of 1-6 carbon atoms (or 2-6 carbons for alkenyl-O—), with higher alkoxy being an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted.

Aryl: An "aryl" is a carbocyclic aromatic system containing one or more rings wherein such rings may be attached together in a pendent manner or may be fused. In particular embodiments, aryl is one, two or three rings. Each ring may contain up to 7 atoms, wherein at least one ring is aromatic. The term "aryl" encompasses aromatic radicals such as phenyl, naphthyl, tetrahydronaphthyl, indanyl, biphenyl, phenanthryl, anthryl or acenaphthyl. The "aryl" group may be optionally substituted.

Phenyl: A "phenyl" is a radical formed by removal of a hydrogen from a benzene ring. The phenyl may be optionally substituted.

Heterocycle: A "heterocycle" or "heterocyclic entity" is a monovalent radical of a 5- or 6-member closed ring containing carbon and at least one other element, generally nitrogen, oxygen, or sulfur and may be fully saturated, partially saturated, or unsaturated (i.e., aromatic in nature). Generally the heterocycle will contain no more than two hetero atoms. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolindinyl, 2- or 3- tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. Representative examples of unsaturated 6-membered hetero-cycles with only one hetero atom include 2-, 3-, or 4-pyridinyl, 2H-pyranyl, and 4H-pyranyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, morpholino, and the like. The corresponding fully saturated and partially saturated radicals are also included, e.g. 2-piperazine. The heterocyclic radical is bonded through an available carbon atom or hetero atom in the heterocyclic ring directly to the entity or through a linker such as an alkylene such as methylene or ethylene. The heterocycle may be optionally substituted.

Optionally substituted: If a radical is referred to as "optionally substituted," it means that the radical may be unsubstituted or at least one hydrogen of the radical may be removed and another substituent inserted in its place. The radical may be optionally substituted with substituents at positions that do not significantly interfere with the preparation of compounds (unless modified after preparation of the enantiomeric precursor) falling within the scope of this invention and that do not significantly adversely affect the biological activity of the compounds. The radical is optionally substituted with one, two, three, four or five substituents independently selected from halo, lower alkoxy, hydroxyl, cyano, nitro, amino, halo lower alkyl, halo lower alkoxy, hydroxycarbonyl, lower alkoxycarbonyl, lower alkylcarbonyloxy, and/or lower alkylcarbonylamino.

Halo: A "halo" substitutent is a monovalent halogen radical chosen from chloro, bromo, iodo, and fluoro. A "halogenated" compound is one substituted with one or more halo substituents.

The term "hydroxycarbonyl" is a monovolent radical having the formula —C(O)OH.

The term "lower alkoxycarbonyl" is a monovalent radical with the formula —C(O)OAlk, where Alk is lower alkyl.

The term "lower alkylcarboxyloxyl" is a monovalent radical with the formula —OC(O)Alk, where Alk is lower alkyl.

As used herein, "a sugar" means a monosaccharide, a disaccharide or a polysaccharide. Suitable monosaccharides include pentose, hexose, or a heptose residue. Non-limiting examples of pentoses include arabinose, ribose, ribulose, xylose, lyxose, and xylulose. Non-limiting examples of hexoses include glucose, galactose, fructose, fucose, mannose, allose, altrose, talose, idose, psicose, sorbose, and tagatose. Non-limiting examples of heptoses include mannoheptulose and sedoheptulose. The sugar moiety may be linked to the compound at any position of the sugar ring which can form an amide or ester bond. Preferred saccharides are beta-glycosyl saccharides.

Certain hepoxilin analogs are designated herein as follows:

PBT-1: racemic anti form of 8-hydroxy-11,12-cyclopropyl-eicosa-5Z,9E,14Z-trienoic acid methyl ester, PBT-2: racemic syn form of 8-hydroxy-11,12-cyclopropyl-eicosa-5Z,9E,14Z-trienoic acid methyl ester;

PBT-3: racemic anti form of 10-hydroxy-11,12-cyclopropyl-eicosa-5Z,8Z,14Z-trienoic acid methyl ester;

PBT-4: racemic syn form of 10-hydroxy-11,12-cyclopropyl-eicosa-5Z,8Z,14Z-trienoic acid methyl ester;

PBT-01: racemic anti form of 8-hydroxy-11,12-cyclopropyl-eicosa-5Z,9E,14Z-trienoic acid;

PBT-02: racemic syn form of 8-hydroxy-11,12-cyclopropyl-eicosa-5Z,9E,14Z-trienoic acid; and PBT-03: racemic anti form of 10-hydroxy-11,12-cyclopropyl-eicosa-5Z,8Z,14Z-trienoic acid.

PBT-04: racemic syn form of 10-hydroxy-11,12-cyclopropyl-eicosa-5Z,8Z,14Z-trienoic acid.

In one embodiment, there is provided a method of separating the racemic hepoxilin analog, PBT-3, into its enantiomers, 10R-hydroxy-11S,12S-cyclopropyl-eicosa-5Z,8Z,14Z-trienoic acid and 10S-hydroxy-11R,12R-cyclopropyl-eicosa-5Z,8Z,14Z-trienoic acid. These compounds are shown in FIG. 1 as their methyl esters, and are designated as Compound A and Compound B, respectively. The PBT-3 is applied to a chiral phase HPLC column. The column is eluted with a solvent comprising hexanes and isopropanol in a ratio of about 99:1 or hexanes and n-butanol in a ratio of about 99.2:0.8 to separate the enantiomers.

Figure 2:
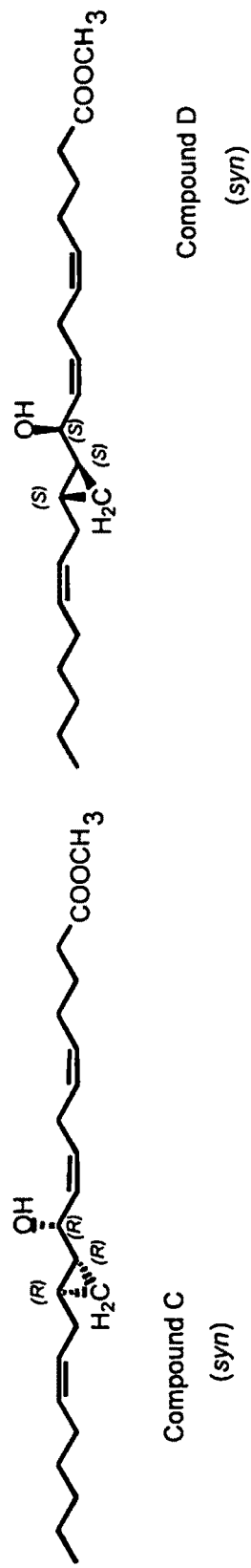
FIG. 2 shows structures of enantiomers of PBT-4.

In a further embodiment, there is provided a method of separating the racemic hepoxilin analog, PBT-4, into its enantiomers 10R-hydroxy-11R,12R-cyclopropyl-eicosa-5Z,8Z,14Z-trienoic acid and 10S-hydroxy-11S,12S-cyclopropyl-eicosa-5Z,8Z,14Z-trienoic acid. These compounds are shown in FIG. 2 as their methyl esters, and are designated as Compound C and Compound D, respectively. The PBT-4 is applied to a chiral phase HPLC column. The column is eluted with a solvent comprising hexanes and isopropanol in a ratio of about 99:1 or hexanes and n-butanol in a ratio of about 99.2:0.8 to separate the enantiomers.

In a further embodiment, there is provided the isolated enantiomers, namely, 10R-hydroxy-11S,12S-cyclopropyl-eicosa-5Z,8Z,14Z-trienoate methyl ester (Compound A in FIG. 1), 10S-hydroxy-11R,12R-cyclopropyl-eicosa-5Z,8Z, 14Z-trienoate methyl ester (Compound B in FIG. 1), 10R-hydroxy-11R,12R-cyclopropyl-eicosa-5Z,8Z,14Z-trienoate methyl ester (Compound C, FIG. 2) and 10S-hydroxy-11S, 12S-cyclopropyl-eicosa-5Z,8Z,14Z-trienoate methyl ester (Compound D, FIG. 2), and their corresponding free acids.

Figure 3:
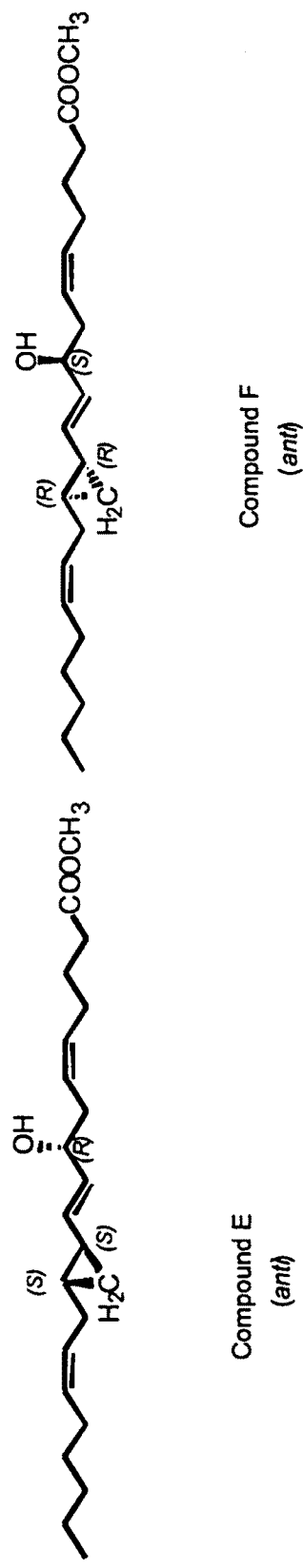
FIG. 3 shows structures of enantiomers of PBT-1.

In a further embodiment, there is provided a method of separating the racemic hepoxilin analog PBT-1 into its enantiomers, 8R-hydroxy-11S,12S-cyclopropyl-eicosa-5Z,9E, 14Z-trienoate methyl ester (Compound E, FIG. 3) and 8S-hydroxy-11R,12R-cyclopropyl-eicosa-5Z,9E,14Z-trienoate methyl ester (Compound F, FIG. 3) and further provides the enantiomers and their corresponding free acids. The PBT-1 is applied to a chiral phase HPLC column. The column is eluted with a solvent comprising hexanes and isopropanol in a ratio of about 99.8:0.2 or hexanes and n-butanol in a ratio of about 99.2:0.8 to separate the enantiomers.

Figure 4:
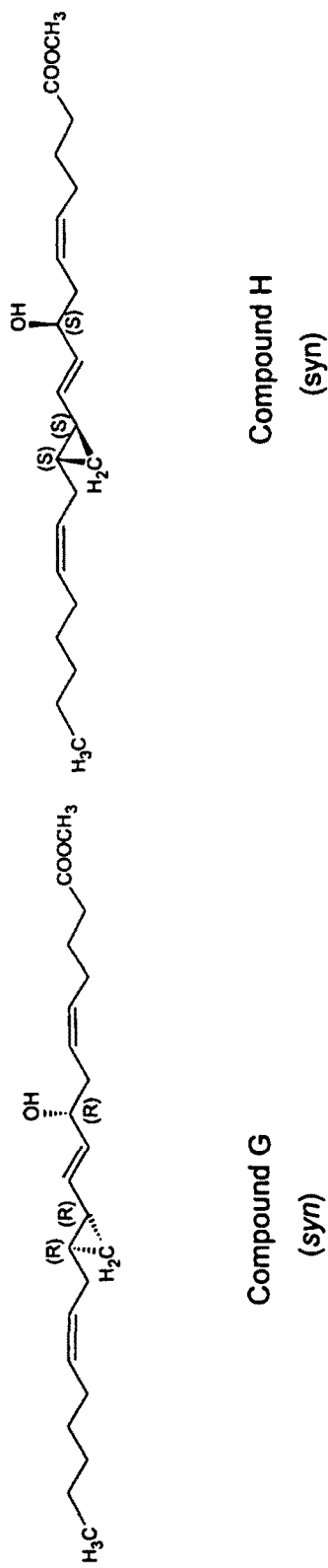
FIG. 4 shows structures of enantiomers of PBT-2.

In another embodiment, there is provided a method of separating the racemic hepoxilin analog PBT-2 into its enantiomers, 8R -hydroxy-11R,12R-cyclopropyl-eicosa-5Z,9E, 14Z-trienoate methyl ester (Compound G, FIG. 4) and 8S -hydroxy-11S,12S-cyclopropyl-eicosa-5Z,9E,14Z-trienoate methyl ester (Compound H, FIG. 4) and further provides the enantiomers and their corresponding free acids. The PBT-2 is applied to a chiral phase HPLC column. The column is eluted with a solvent comprising hexanes and n-butanol in a ratio of about 99.2:0.8 to separate the enantiomers. Isopropanol/hexanes did not afford good separation of these enantiomers.

Pharmaceutically acceptable salts of the described compounds, as discussed above, are also provided.

In general, with respect to a method for separating a racemic hepoxilin analog into its enantiomers, the racemic hepoxilin analog is first applied to a chiral phase HPLC column. The column is eluted with a solvent to separate the enantiomers, typically, a mixture of at least one non-polar solvent and at least one polar solvent. For example, the solvent comprises at least one alkane and at least one alcohol. Typical alkanes include any suitable alkanes such as, and without being limited thereto, pentanes, hexanes, heptanes, branched and/or linear. Typical alcohols include any suitable alcohols such as, and without being limited thereto, methanol, ethanol, n-propanol, isopropanol, n-butanol, sec-butanol, and/or tert-butanol. When an alcohol is immiscible in the chosen alkane(s), an additional ternary solvent may be used, such as, and without being limited thereto, diethyl ether, acetone, and/or dimethoxy propane, to solubilize the alcohol in the alkane(s). Typically, the solvent system chosen provides baseline separation of the enantiomers.

Some examples of chiral phase HPLC columns include Chiralcel OD column—DAICEL Chemical Ind.—CSC, Montreal, 10 micron particle size, and Chiralcel OD-H column—DAICEL Chemical Ind.—CSC, Montreal, 5 micron particle size.

Typical ranges of solvents include about 99.9:0.1 to about 90:10 of the alkane(s) (e.g. hexane) to alcohol(s). More typical ranges include about 99.5:0.5 to about 95:5; about 99.5: 0.5 to about 97:3; about 99:1 to about 98:2; and about 99.8:0.2 to about 99.5:0.5, depending on the polarity of the compound to be resolved. For example, the free carboxylic acid is more polar than the methyl ester thereof.

Compound A was twice as potent as racemic PBT-3 with respect to inhibition of platelet aggregation evoked by the thromboxane agonist, I-BOP. (See example 5). Compound A was also 1.3 times more potent than the racemate with respect to inhibition of cell proliferation, and was about four times more potent than compound B in the platelet aggregation assay and about 2-fold more potent in the inhibition of cell proliferation. (See Example 6). Compound B was 1.6 to 1.9 fold less active than the racemate and may have an antagonistic effect against compound A when both are present, as in the racemic mixture.

Example 6a shows compound A was more active than Compound B in inducing cleavage of caspase-3 in K562 cells in vitro. The enantioselectivity between Compounds C and D was less than that between Compounds A and B.

Therefore, a more potent hepoxilin analog in the form of the purified enantiomer compound A is provided. It is expected in light of the above results that compound A will also show increased activity compared to the racemate with respect to other biological activities demonstrated for the racemate and related hepoxilin analogs. These biological activities include inhibition of inflammation (Jankov et at., (2000); International Patent Application No. WO 01/010422), stimulation of insulin release (International Patent Application No. WO 01/010422), inhibition of stimulation of intracellular calcium (U.S. Pat. No. 5,616,607), inhibition of thromboxane formation and action (International Patent Application No. WO 02/38157, Pace-Asciak et al., 2002), inhibition of proliferation of neoplastic cells (International Patent Application No. WO 03/099285), and inhibition of solid tumour growth (Li et al., (2005); Pace-Asciak et at., (2006)).

Compounds C and D showed fairly similar levels of activity to each other and to the racemic mixture with respect to inhibition of platelet aggregation and inhibition of cell proliferation. In both assays, Compound C was more active than Compound D by 1.4 fold (platelet aggregation assay) and 1.3 fold (cell proliferation assay). However, as can be seen in Example 10 below, Compound D appears to activate PPAR gamma activation of a gene more effectively than Compound C. It is likely that the 'anti' relative configuration of hydroxyl vs. cyclopropyl groups (as in Compounds A and B) will be more active than the 'syn' relative configuration (as in Compounds C and D) and will possess a greater degree of enantioselectivity.

Compound F showed significantly more activity than Compound E or the racemic mixture of PBT-1 in PPAR gamma transactivation of gene expression. This makes Compound F a particularly interesting candidate as a therapeutic to treat PPAR-mediated conditions, in particular PPAR gamma-mediated conditions described in more detail hereinbelow.

The enantiomer separation and characterisation methods of the invention are expected to be effective with the hepoxilin analogs described herein. Once isolated, the enantiomers may be chemically or enzymatically modified, for example to include substituents of interest, such as halogen or sugar residues, and other residues referred to in more detail herein, or to be converted to carboxylate salts with improved pharmaceutical properties.

It is noted that the enantiomers with improved biological activity in for example, platelet aggregation and inhibition of cell proliferation, namely Compounds A and C, possess a configuration that is unexpected in comparison to the biologically active natural hepoxilins (Demin, Reynaud et al., 1995). The latter are derived from 12S-lipoxygenase and possess an epoxide configuration of 11S,12S and S configuration at the C8 or C10 hydroxyl group. Compound A on the other hand has the cyclopropyl groups at 11S,12S, with a hydroxyl group at 10R, while the configuration of the cyclopropyl group of Compound C is 11R,12R and the hydroxyl group is at 10R. The results described herein indicate that the 10R configuration of the carbinolic centre provides the enantiomer with better biological activity than the 10S enantiomers. In light of the present specification, one would expect the same behaviour of the compounds with the C8 carbinolic centre.

In a general embodiment, there is provided a compound of formula:

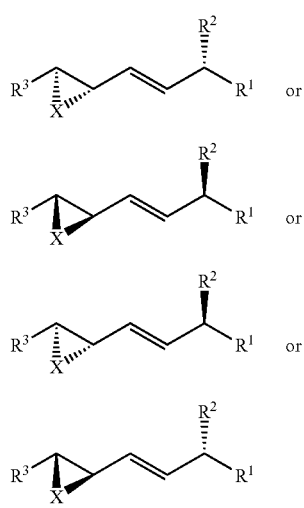

wherein,

X is O, CH$_2$, NH, S, N-alkyl, (CH$_2$)$_n$ where n is 2, 3 or 4, or (CH$_2$)$_m$—Y, where Y is S, NH or O and m is 1, 2 or 3;

R$^1$ is lower alkyl, alkenyl or alkynyl; lower alcohol, saturated or unsaturated; aryl; substituted aryl; —(CH$_2$)n-phenyl where n is 1 to 9; or Z—R$^5$, wherein Z is a single bond or a C1-C10 carbon chain optionally substituted with —OH and/or halogen and/or optionally containing up to three double or triple bonds or a mixture of double and triple bonds up to a maximum of three; and R$^5$ is C1-C10 alkyl OH, C1-C10 alkyl-halide, C1-C10 alkyl N3, C1-C10 alkyl —NH2 or COOR$^6$ or CONHR$^6$, and preferably R$^5$ is COOR$^6$ or CONHR$^6$, wherein R$^6$ is H, C5 or C6 cycloalkyl, C5-C6 aryl, a sugar moiety or C1-C10 alkyl or alkenyl optionally substituted with COOH, C5-C6 aryl, heterocycle or a sugar moiety, and preferably R$^6$ is CH$_3$, H, alkyl substituted with COOH or a heterocycle;

R$^2$ is H, OH, halogen, NH$_2$, SH, OPO$_3$H, lower alkyl, alkenyl or alkynyl, lower alcohol, O-lower alkyl or alkenyl, S-lower alkyl or alkenyl, NH-lower alkyl or alkenyl, or N bis-lower alkyl or alkenyl; and R$^3$ is a C4-C15 carbon chain optionally substituted with —OR$^7$, wherein R$^7$ is H, lower alkyl, alkenyl or alkynyl; and preferably R$^3$ is an unsubstituted C4 to C10 chain wherein R$^3$ optionally contains up to three double or triple bonds or a mixture of double and triple bonds up to a maximum of three;

or a pharmaceutical salt thereof.

In accordance with another general embodiment, there is provided a compound of formula:

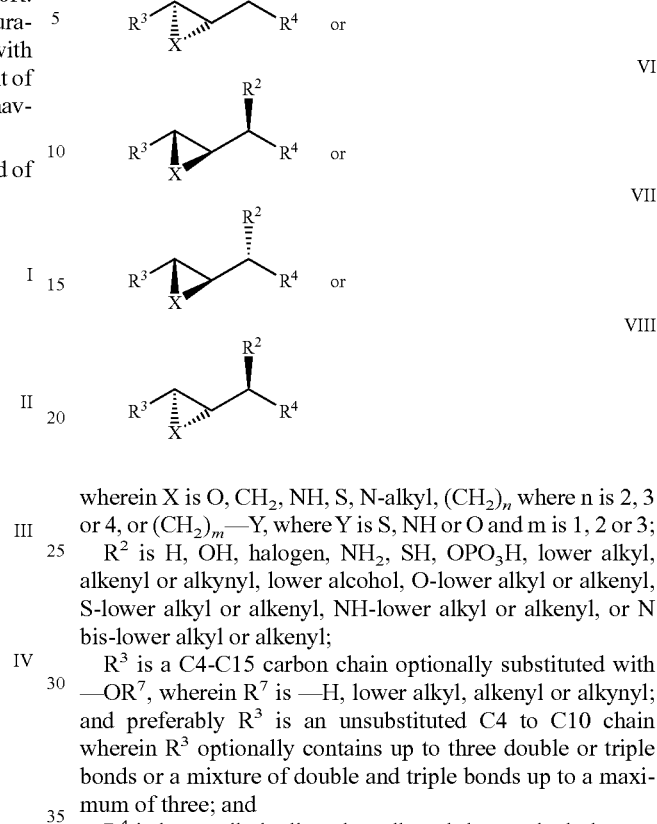

wherein X is O, CH$_2$, NH, S, N-alkyl, (CH$_2$)$_n$ where n is 2, 3 or 4, or (CH$_2$)$_m$—Y, where Y is S, NH or O and m is 1, 2 or 3;

R$^2$ is H, OH, halogen, NH$_2$, SH, OPO$_3$H, lower alkyl, alkenyl or alkynyl, lower alcohol, O-lower alkyl or alkenyl, S-lower alkyl or alkenyl, NH-lower alkyl or alkenyl, or N bis-lower alkyl or alkenyl;

R$^3$ is a C4-C15 carbon chain optionally substituted with —OR$^7$, wherein R$^7$ is —H, lower alkyl, alkenyl or alkynyl; and preferably R$^3$ is an unsubstituted C4 to C10 chain wherein R$^3$ optionally contains up to three double or triple bonds or a mixture of double and triple bonds up to a maximum of three; and R$^4$ is lower alkyl, alkenyl or alkynyl; lower alcohol, saturated or unsaturated; aryl; substituted aryl: —(CH$_2$)$_n$-phenyl where n is 1 to 9; or Z—R$^5$, wherein Z is a single bond or a C1-C10 carbon chain optionally substituted with —OH and/or halogen and/or optionally containing up to three double or triple bonds or a mixture of double and triple bonds up to a maximum of three; and R$^5$ is C1-C10 alkyl OH, C1-C10 alkyl-halide, C1-C10 alkyl N3, C1-C10 alkyl —NH2 or COOR$^6$ or CONHR$^6$, and preferably R$^5$ is COOR$^6$ or CONHR$^6$, wherein R$^6$ is H, C5 or C6 cycloalkyl, C5-C6 aryl, a sugar moiety or C1-C10 alkyl or alkenyl optionally substituted with COOH, C5-C6 aryl, heterocycle or a sugar moiety, and preferably R$^6$ is —CH$_3$, —H, alkyl substituted with COON or a heterocycle.

In accordance with a further embodiment, there is provided isolated enantiomeric forms of racemic hepoxilin analogs of the formula I, II, II or IV, wherein:

X is O, CH$_2$, S or NH;

R$^1$ is COOH, lower alkyl, lower alkenyl, lower alkynyl, aryl, substituted aryl, —(CH$_2$)$_n$-phenyl where n is 1 to 9; lower alkoxy, saturated or unsaturated; —CH$_2$CH═CH—(CH$_2$)$_3$—COR$^8$ wherein R$^8$ is OH, O-lower alkyl or alkenyl; COOR$^6$ or CONHR$^6$, wherein R$^6$ is CH$_3$or a sugar moiety;

R$^2$ is OH, NH$_2$, SH, OPO$_3$H, lower alkyl or alkenyl; or O-lower alkyl or alkenyl; or N-lower alkyl or alkenyl; or S-lower alkyl or alkenyl; and R$^3$ is lower alkyl, alkenyl or alkynyl; or —CH$_2$—CH═CH—(CH$_2$)$_4$—R$^9$ wherein R$^9$ is CH$_3$, CH$_2$OH, CH$_2$—O-lower alkyl or alkenyl, aryl or substituted aryl, or (CH$_2$)$_n$-phenyl where n is 1 to 9;

or a pharmaceutical salt thereof;

with the proviso that if $R^2$ is OH, and $R^1$ is —$CH_2CH=CH$—$(CH_2)_3$—COOH or —$CH_2CH=CH$—$(CH_2)_3$—$COOCH_3$ and $R^3$ is —$CH_2$—$CH=CH$—$(CH_2)_4$—$CH_3$, then X is not O.

In accordance with yet a further embodiment, there is provided a compound of the formula V, VI, VII or VIII as defined above, wherein:

X is O, $CH_2$, S or NH;

$R^2$ is OH, $NH_2$, SH, $OPO_3H$, lower alkyl or alkenyl; or O-lower alkyl or alkenyl; or N-lower alkyl or alkenyl; or S-lower alkyl or alkenyl;

$R^3$ is lower alkyl, alkenyl or alkynyl; or —$CH_2$—$CH=CH$—$(CH_2)_4$—$R^9$ wherein $R^9$ is $CH_3$, $CH_2OH$, $CH_2$—O-lower alkyl or alkenyl, aryl or substituted aryl, or $(CH_2)_n$-phenyl where n is 1 to 9; and $R^4$ is lower alkyl, alkenyl or alkynyl; lower alkoxy, saturated or unsaturated; or —$CH=CH$—$CH_2$—$CH=CH$—$(CH_2)_3$—$COR^8$ wherein $R^8$ is OH, O-lower alkyl or alkenyl; $COOR^6$ or $CONHR^6$, wherein $R^6$ is $CH_3$ or a sugar moiety;

or a pharmaceutical salt thereof;

with the proviso that if $R^2$ is OH and $R^3$ is —$CH_2$—$CH=CH$—$(CH_2)_4$—$CH_3$ and $R^4$ is —$CH=CH$—$CH_2$—$CH=CH$—$(CH_2)_3$—COON or —$CH=CH$—$CH_2$—$CH=CH$—$(CH2)_3$—$COOCH_3$, then X is not O.

In a further embodiment, substituted aryl in the above-described formulae is phenyl substituted with OH, I, Br, Cl or lower alkyl or alkenyl.

The hepoxilin analog enantiomers described herein can be used to inhibit thromboxane formation and antagonize thromboxane activity in mammals. Example 5 below illustrates these effects. There is considerable interest in finding ways of selectively controlling thromboxane formation, so as to inhibit vasoconstriction and platelet aggregation. Thromboxane $A_2$ is a powerful vasoconstrictor and also a potent mediator of platelet aggregation through the activation of the thromboxane receptors. Hence thromboxane receptor antagonists, such as the enantiomers of the present invention (in particular Compound A and Compound C) are useful to treat thromboxane-mediated diseases including cardiovascular diseases, diabetes mellitus, hypertension, thrombosis and septic shock, or any disorder where it is desirable to reduce thromboxane formation and/or activity.

The hepoxilin analog enantiomers can also modulate intracellular calcium concentration, for example inhibiting agonist-induced changes in the free intracellular calcium concentration of neutrophils and thereby allowing control of inflammation and infection. Calcium-regulated cell signaling pathways also regulate other cellular functions, such as smooth muscle contraction, thereby allowing control of aortic and tracheal vasoconstriction and of vascular permeability, for example.

Peroxisome proliferator-activated receptors (PPARs) are nuclear hormone receptors that regulate gene transcription in response to peroxisome proliferators and fatty acids. PPARs also play an important role in the regulation of adipocyte differentiation. It is unclear, however, what naturally occurring compounds activate each of the PPAR subtypes. PPARs play an important role in many cellular functions including lipid metabolism, cell proliferation, differentiation, adipogenesis and inflammatory signaling. PPARs have been found to interact with a number of endogenous lipids and drugs for the treatment of human metabolic diseases. There are three distinct PPAR subtypes that are the products of different genes and are commonly designated PPAR alpha [NR1C1], PPAR beta (also known as PPAR delta) [NR1C2] and PPAR gamma [NR1C3]. Each receptor shows a differential pattern of tissue expression and is activated by structurally diverse compounds. PPAR gamma is the target of thiazolidinediones, a class of antidiabetic drugs that function as direct ligands for PPAR gamma and which are adipogenic (Kliewer et al, 1995; Spiegelman, B. M. 1998). PPAR gamma is expressed only in adipose tissue (Tontonoz et al, 1994), and activators of PPAR can induce adipose conversion of preadipocyte cell lines (Chawla and Lazar, 1994).

The hepoxilin analog enantiomers of the invention also act as PPAR modulators, in particular PPAR gamma agonists and therefore are capable of serving as pharmaceuticals for controlling the biological effects of PPAR mediated transcriptional control and the attendant physiological effects produced thereby. A PPAR gamma agonist is a compound or composition which potentiates, stimulates, induces or otherwise enhances the transcriptional activity of a PPAR gamma receptor, e.g., by mimicking (at least partially) a natural physiological ligand for the receptor. Receptor modulating activity can be easily determined by any number of methods known in the art or adaptations thereof. For example, PPAR modulating activity may be determined by a transactivation assay, such as that described in Example 9.

Example 10 below illustrates that each enantiomer of PBT-1, PBT-2, PBT-3 and PBT-4 and their respective methyl esters show PPAR gamma transactivation activity, Compound F shows significantly better PPAR gamma transactivation activity (indicative of an agonist) than Compound E and its racemate (PBT1). Although the activity of Compound A and Compound B seem very similar in PPAR gamma transactivation studies, Compound B is believed to have better binding to PPAR gamma than Compound A and is therefore likely to have better PPAR gamma modulating activity than Compound A. Example 10 further shows Compound D to have improved PPAR gamma transactivating activity over Compound C. Thus, each of Compounds A-F are useful candidates in treating PPAR-mediated conditions described herein, in particular Compounds F, B and D, and most preferably Compound F.

Thus, the hepoxilin analog enantiomers described herein can be used in pharmaceutical compositions and methods for treatment of a variety of clinical conditions. Such conditions include, but are not limited to, viral infection, microbial infection, cancer, autoimmune disease, inflammatory diseases, ocular disease, septic shock, asthma, ichthyosis, cardiovascular disease, thrombosis, migraine, metabolic syndrome and diabetes.

The clinical condition may therefore be an infection, such as a viral infection, notably AIDS or infection by HIV or infection by the hepatitis C virus, or a microbial infection.

The clinical condition may be cancer, where in particular the inhibition of proliferation of neoplastic cells or solid tumour growth is desired. The cancer may, for example, be any of the following: carcinomas, sarcomas, leukemias, and lymphomas; tumor angiogenesis and metastasis; skeletal dysplasia; hepatic disorders; and hematopoietic and/or myeloproliferative disorders. Exemplary disorders include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

In some embodiments, the cancer is one of the above-mentioned cancers where activation of PPAR gamma and any of the hepoxilin analog enantiomers with PPAR modulating activity, in particular Compound C can be used to inhibit cell proliferation of said cancers or in the preparation of a medicament to treat said cancers. Thus, the clinical condition may, for example, be a disorder characterized by aberrant cell growth of PPAR-responsive cells such as hyperplastic or neoplastic disorders arising in adipose tissue, such as adipose cell tumors, e.g., lipomas, fibrolipomas, lipoblastomas, lipomatosis, hibernomas, hemangiomas, and/or liposarcomas. Furthermore, certain cancers of prostate, stomach, lung and pancreas have been demonstrated to be responsive to treatment with PPAR gamma agonists. In particular, certain liposarcomas, prostate cancers, multiple myelomas, and pancreatic cancers have been shown to be responsive to activation of PPAR gamma, whereas at least some colorectal and breast cancers are not responsive (Rumi et al., (2004)). Other studies have demonstrated that other breast and colon cancers are responsive to PPAR agonists, as well as neuroblastoma and bladder cancers. The use of PPAR ligands for treatment of certain cancers is reviewed by Kopelovich et al., (2002), the teachings of which may be applied to the hepoxilin analog enantiomers described herein, in particular Compound B.

The clinical condition may also be a liver disease, in particular those responsive to PPAR modulation, notably infection by the hepatitis C virus, or fatty liver, liver inflammation, liver lesions, liver cirrhosis, or post-hepatic cancer, whether or not associated with a hepatitis C virus infection.

The clinical condition may also be an autoimmune diseases including without limitation asthma, multiple sclerosis, psoriasis, topical dermatitis, and ulcerative colititis.

The clinical condition may be an inflammatory disease including both acute and chronic inflammatory disorders, where in particular inhibition of inflammation is desired. For example, the inflammatory disease may be inflammatory bowel disease, ulcerative colitis, or Crohn's disease. The inflammatory disorder may also be arthritis, notably rheumatoid arthritis and polyarthritis, an inflammatory skin disease, notably acne vulgaris, atopic dermatitis, cutaneous disorders with barrier dysfunction, cutaneous effects of aging or psoriasis, or septic shock. The inflammatory disorder may also be an inflammatory neurodegenerative disease, such as multiple sclerosis or Alzheimer's disease.

In some embodiments, the clinical condition is an inflammatory disorder mediated by PPAR gamma, ie. PPAR gamma plays a role in the manifestation of the condition, which is typically a chronic inflammatory disorder. In contrast, PPAR gamma is considered not to play a role in inflammation associated with neutrophil activation, such as acute inflammations.

The clinical condition may also be an ocular disease, in particular those associated with ocular inflammation and/or increased ocular pressure.

The clinical disease may be ichthyosis, a skin disorder characterized by the presence of excessive amounts of dry surface scales. Ichthyosis is a disorder of keratinization or cornification, and it is due to abnormal epidermal differentiation or metabolism, which can sometimes also be linked to ocular diseases.

The clinical condition may be a cardiovascular diseases, such as, hypertension, thrombosis, stroke, atherogenesis, atherosclerosis or an atherosclerotic disorder, vascular restinosis, cardiomyopathy, or myocardial fibrosis, or migraine.

The clinical condition may also be a gastrointestinal disease or a renal disease, including glomerulonephritis, glomerulosclerosis, nephritic syndrome, and hypertensive nephrosclerosis, sodium retention by the kidneys or prevention of damage to blood vessels and kidneys.

The clinical condition may also be diabetes, in particular Type II diabetes, or Non Insulin Dependent Diabetes Mellitus (NIDDM). Diabetes mellitus refers to a disease process derived from multiple causative factors and characterized by elevated levels of glucose in blood, or hyperglycemia. NIDDM is a complex disease derived from multiple causative factors, which can be addressed in some cases by increasing circulating insulin levels. The hepoxilin analog enantiomers of the invention may be used to increase insulin secretion/reduce hyperglycemia.

The clinical condition may also be insulin resistance and related conditions. Insulin resistance is the diminished ability of insulin to exert its biological action in the body across a broad range of concentrations. During early stages of insulin resistance, the body secretes abnormally high amounts of insulin to compensate for this defect. Even though blood insulin levels are chronically high, the impaired metabolic response of active muscle cells to insulin make them unable to take up glucose effectively. Insulin resistance and the resulting hyperinsulinemia contribute to several clinical conditions, including metabolic syndrome (also designated syndrome X). Patients with metabolic syndrome suffer from hyperinsulinemia, dyslipidemia and reduced glucose tolerance, and are at an increased risk of developing cardiovascular disease and/or type II diabetes. The hepoxilin analog enantiomers of the present invention with PPAR gamma agonist activity, in particular Compound C is particularly useful for such treatment, and increasing insulin sensitivity. Such treatment may be used for chronic disease, or acute and transient disorders in insulin sensitivity, such as those that may occur following trauma, surgery, or myocardial infarction. The hepoxilin analog enantiomers or derivatives thereof may be involved in reducing glucose plasma levels independently of changes in insulin levels, i.e. insulin levels may decrease secondary to the lowering of plasma glucose.

The clinical condition according to the present invention may also be hyperlipidemia, such as familial hyperlipidemia. Preferably, hyperlipidemia is characterised by hypercholesterolemia and/or hypertriglyceridemia. The clinical condition may also include dyslipidemia and diabetic dyslipidemia. The hepoxagen analog enantiomers may also be utilized to lower serum triglyceride levels or raise the plasma level of HDL, and other lipid metabolism disorders.

Modulators of PPAR activity, including the hepoxilin analog enantiomers of the invention, may also be employed in weight control (eg, by affecting adipose tissue). Activation of PPAR gamma can contribute to adipocyte differentiation by activating the adipocyte-specific gene expression (Lehmann et al., (1995)). Thus, a PPAR gamma agonist can be used to gain fatty tissue. Some PPAR gamma partial agonists may only activate a subset of genes, and can therefore be selected for properties useful in treating excessive build-up of fatty tissue, e.g., no adipocyte differentiation and/or increased energy expenditure, allowing the treatment of obesity.

Although much of the description above relating to PPAR has focused on PPAR gamma, the hepoxilin analog enantiomers may be used to modulate other PPAR subtypes that play an important role in disease. For example, PPAR delta has been associated with lipid metabolism disorders and wound healing, in particular epidermal wound healing (Tan et al., (2003)). Thus, the clinical condition may also be wound healing, including epidermal wound healing.

In addition, PPAR agonists of the invention may be useful for improving cognitive functions in neurological diseases or in dementia or for treating polycystic ovarian syndrome or for preventing and treating bone loss, e.g., osteoporosis.

The present invention relates to methods of treatment of any of the clinical conditions referred to hereinabove comprising administration of above-mentioned hepoxilin analog enantiomers or pharmaceutically acceptable salts thereof to an individual in need thereof, as well as to uses of said enantiomers for the preparation of a medicament for treatment of the clinical conditions referred to hereinabove. In accordance with the methods of treatment and compositions of the present invention, one or more hepoxilin analog enantiomers may be administered to a mammal, including a human, in a variety of forms depending on the selected route of administration, as will be understood by those skilled in the art.

The compositions of the invention may be administered orally or parenterally, the latter route including intravenous, intraperitoneal and subcutaneous administration. Parenteral administration may be by continuous infusion over a selected period of time. Forms for injectable use include sterile aqueous solutions or dispersion and sterile powders for the extemporaneous preparation of sterile injectable solutions or dispersions. In all cases the form must be sterile and must be fluid to permit easy syringability.

In a further embodiment, one or more hepoxilin analog enantiomers may be administered intra-ocularly. Compositions for intra-ocular use include eye drops comprising the compound dissolved in a fluid acceptable for intra-ocular administration, for example physiological saline.

For ease of administration by the patient, oral or other non-invasive modes of administration are preferred, e.g. patches, suppositories and the like. The hepoxilin analog enantiomer may be orally administered with an inert diluent or with an assimilable edible carrier, or it may be enclosed in hard or soft shell gelatin capsules, compressed into tablets or incorporated directly with the food of the diet. For oral therapeutic administration, a hepoxilin analog enantiomer may be incorporated with excipient and used in the form in ingestible tablets, buccal tablets, troches, capsules, elixirs, suspensions, syrups, wafers and the like.

Compositions containing one or more hepoxilin analog enantiomers described herein can also be administered in a solution or emulsion contained within phospholipid vesicles called liposomes. The liposomes may be unilamellar or multilamellar and are formed of constituents selected from phosphatidylcholine, dipalmitoylphosphatidylcholine, cholesterol, phosphatidylethanolamtine, phosphatidylserine, dimyristoylphosphatidylcholine and combinations thereof. The multilamellar liposomes comprise multilamellar vesicles of similar composition to unilamellar vesicles, but are prepared so as to result in a plurality of compartments in which the analogs containing solution or emulsion is entrapped. Additionally, other adjuvants and modifiers may be included in the liposomal formulation such as polyethyleneglycol, or other materials.

The liposomes containing the hepoxilin analog enantiomer compositions may also have modifications such as having antibodies immobilized on the surface of the liposome in order to target their delivery.

In an embodiment, there is provided a pharmaceutical composition comprising the above-mentioned hepoxilin analog enantiomers or pharmaceutically acceptable salts thereof for administration to subjects in a biologically compatible form suitable for administration in vivo for treating a disorder associated with an increased level of thromboxane or a disorder wherein it is desirable to reduce thromboxane activity, including but not limited to inflammatory disorders, thrombosis, stroke or diabetes.

The compositions of the invention comprise a safe and therapeutically effective amount of a hepoxilin analog enantiomer alone, or in combination with other agents and pharmaceutical carriers. The composition may be administered to any living organism in need of such treatment including humans and animals as the composition has efficacy in vivo. By safe and effective, as used herein, is meant providing sufficient potency in order to decrease, prevent, ameliorate or treat the condition affecting the subject while avoiding serious side effects. A safe and effective amount will vary depending on the age of the subject, the physical condition of the subject being treated, the severity of the clinical condition, the duration of treatment and the nature of any concurrent therapy, and its determination is within the skill of the ordinary physician.

A therapeutically effective amount of a pharmaceutical composition of the present invention means an amount effective, at dosages and for periods of time necessary to achieve the desired result. This may also vary according to factors such as the disease state, age, sex, and weight of the subject and the ability of the hepoxilin analog enantiomer to elicit a desired response in the subject. The hepoxilin analogs described previously have been shown to be non-toxic and well tolerated in animal studies at concentrations up to 40 mg/kg and it is expected that the active enantiomers described herein are at least as well tolerated. A dose of around 0.1 to 50mg/kg is likely a suitable initial dosage for a mammal and this dosage may be adjusted as required to provide a safe and effective amount. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems having innocuous physiological reactions when administered to a subject. Some examples include but are not limited to starches, sugars, cellulose and its derivatives, powdered tragacanth; malt, gelatin, talc, stearic acids, magnesium stearate, calcium sulfate, vegetable oils, polyols, agar, alginic acids, pyrogen free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the hepoxilin analog enantiomer is combined in a mixture with a pharmaceutical acceptable carrier. Suitable carriers are described for example in Remington's Pharmaceutical Sciences (Mack Publishing Company, Easton, Pa., USA, 1985). The compositions may include solutions of one or more hepoxilin analog enantiomers in association with one or more pharmaceutical acceptable vehicles or diluents, and contained in buffered solutions with a suitable pH and iso-osmotic with the physiological fluids.

A pharmaceutical composition may comprise the above-mentioned hepoxilin analog enantiomers or pharmaceutically acceptable salts thereof for administration to subjects in a biologically compatible form suitable for administration in vivo for treating a disorder or clinical condition described above. The method comprises a safe and effective amount of a compound alone, or in combination with other agents and/or pharmaceutical carriers. For example, the hepoxilin analog enantiomers described herein may be used to treat insulin resistance and/or diabetes in combination with an agent effective against dislipidemia, such as a drug of the fibrate class, e.g., Bezafibrate. The examples of some other agents are insulin sensitizers, PPARy agonists, glitazones, troglitazone, pioglitazone, englitazone, MCC 555, BRL.49653, biguanides, metformin, phenformin, insulin, insulin minetics, sufonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrates, cholestyramine, colestipol, dialkylaminoalkyl derivatives of a cross-linked dextran, nicotinyl alcohol, nicotinic acid: a nicotinic acid salt, PPARalpha agonists, fenofibric acid derivatives, gemfibrozil, clofibrate, fenofibrate, inhibitors of cholesterol absorption, beta-sitosterol, acryl CoA:cholesterol acyltransferase inhibitors, melinamide, probucol, PPARdelta agonists, antiobesity compounds, fenfluramine, dexfenfluramine, phentiramine, sulbitramine, orlistat, neuropeptide Y5 inhibitors, β3 adrenergic receptor agonists, and ileal bile acid transporter inhibitors. The hepoxilin analog enantiomers of the invention may also be used to treat cancer in combination with, for example, anti-angiogenesis agents, signal transduction inhibitors, cytotoxic agents and/or antiproliferative agents, which amounts are together effective in inhibiting abnormal cell growth.

The composition may be administered to any living organism in need of such treatment including humans and animals as the composition has efficacy in vivo. By safe and effective, as used herein, is meant providing sufficient potency in order to decrease, prevent, ameliorate, or treat the disease affecting the subject while avoiding serious side effects. A safe and effective amount will vary depending on the age of the subject, the physical condition of the subject being treated, the severity of the disorder, the duration of treatment and the nature of any concurrent therapy, and its determination is within the skill of the ordinary physician. The compositions are formulated and administered in the same general manner as described herein. The compounds of the present invention may be used effectively alone or in combination with one or more additional active agents. Combination therapy includes administration of a single pharmaceutical dosage composition, which contains a compound of the present invention and one or more additional active agents, as well as administration of a compound of the present invention and each active agent in its own separate pharmaceutical dosage. For example, a compound of the present invention and an insulin secretogogue such as sulfonylureas, thiazolidinediones, biguanides, meglitinides, insulin or alpha-glucosidase inhibitors can be administered to the patient together in a single oral dosage composition such as a capsule or tablet, or each agent administered in separate oral dosages. Where separate dosages are used, a compound of the present invention and one or more additional active agents can be administered at essentially the same time, i.e., concurrently or at separately staggered times, i.e., sequentially; combination therapy is understood to include all these regimens.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof. The terms "comprising", "having", "including" are intended to be open-ended and mean that there may be additional elements other than the listed elements.

The above disclosure generally describes the present invention. A more complete understanding can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Methods of chemical synthesis and analysis and biochemistry referred to but not explicitly described in this disclosure and examples are reported in the scientific literature and are well known to those skilled in the art. The hepoxilin analog racemate methyl esters described herein were typically prepared as described in U.S. Pat. No. 5,616,607. The diastereoisomers are separated (e.g. syn from anti) by HPLC before separation of the enantiomers as described below.

Example 1

Separation of 10R-hydroxy-11S,12S-cyclopropyl-eicosa-5Z,8Z,14Z-trienoic acid methyl ester (anti) (Compound A) from racemic PBT-3

Racemic anti form of 10-hydroxy-11,12-cyclopropyl-eicosa-5Z,8Z,14Z-trienoic acid methyl ester (PBT-3) was prepared and isolated as described in U.S. Pat. No. 5,616,607. This example describes the isolation of the respective enantiomers from the racemic mixture.

Attempts to separate the enantiomers of PBT-3 by conventional methods involving HPLC (on normal and reverse supports) were unsuccessful.

The enantiomeric separation of racemic PBT-3 was successfully carried out on a chiral phase HPLC column (Chiralcel OD column—DAICEL Chemical Ind.—CSC, Montreal, 10 micron particle size), using hexanes-isopropanol about 99:1 v/v, and a flow rate of 1 ml/min. The column allowed the separation of 50-100 micrograms at a time, affording pure enantiomers.

The racemate PBT-3 gave two products, compound A and compound B, in a 1:1 ratio. Compound A (10R-hydroxy-11S, 12S-cyclopropyl-eicosa-5Z,8Z,14Z-trienoic acid methyl ester, FIG. 1) was well separated from its mirror image and eluted at 18.2 min.

The enantiomeric separation of racemic PBT-3 was also successfully carried out on a chiral phase HPLC column (Chiralcel OD column—DAICEL Chemical Ind.—CSC, Montreal, 10 micron particle size), using hexanes and n-butanol about 99.2:0.8 v/v, and a flow rate of 1.5 ml/min. The column allowed the separation of 50-100 micrograms at a time, affording pure enantiomers.

The racemate PBT-3 gave two products, compound A and compound B. Compound A was well separated from its mirror image and eluted at 12.4 min.

Figure 5:
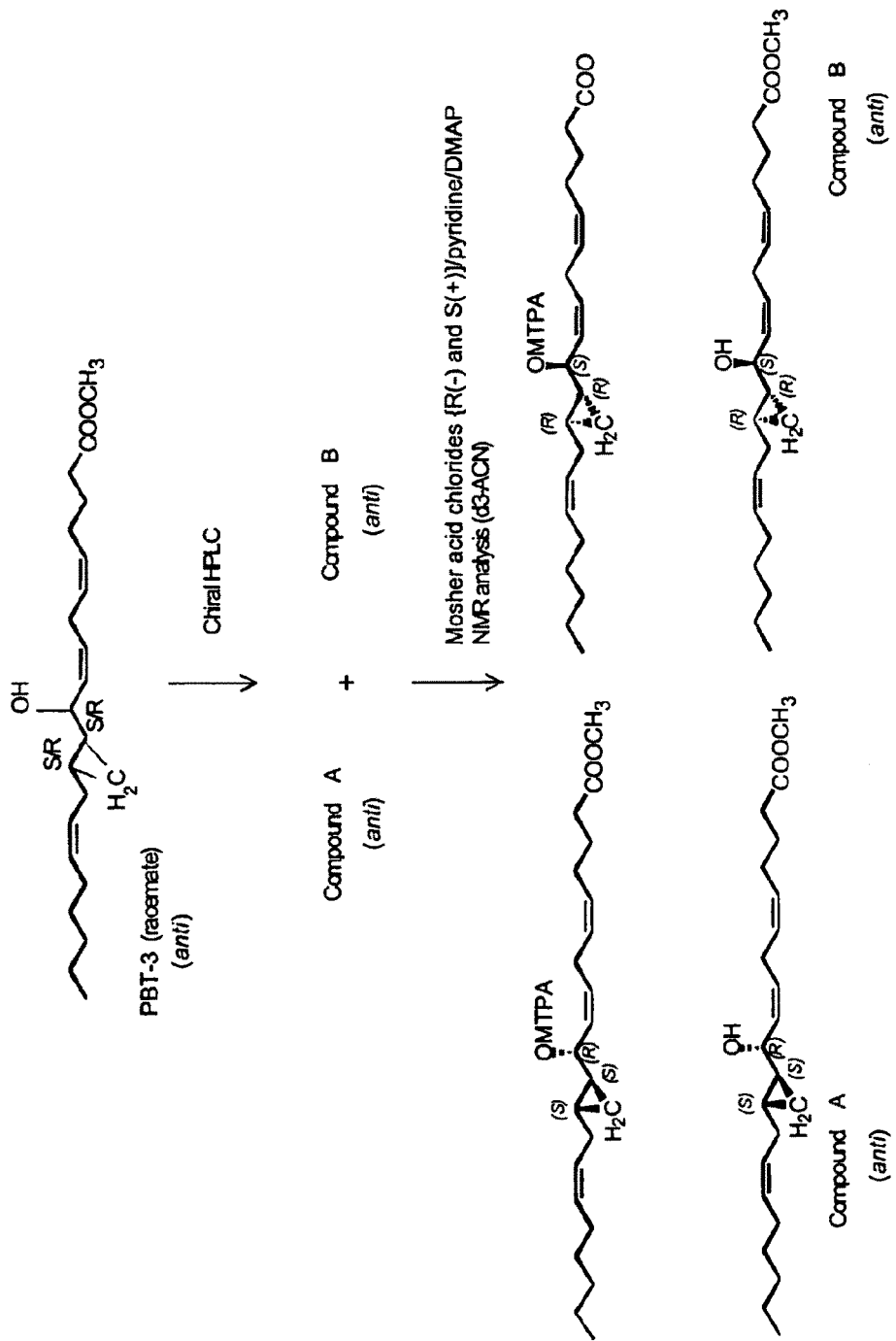
FIG. 5 shows a process used to characterise Compounds A and B.

The absolute configuration of the C10 carbinolic centre of compound A was established through conversion of the pure enantiomer into a Mosher ester with commercially available chirally pure R and S Mosher acid chlorides and analysis of the Mosher ester derivative by NMR. Unlike the situation with the natural hepoxilin compounds, the preparation of the Mosher esters from the acid chloride reagent presented unexpected difficulties as compound A was unstable in the alkaline conditions of the reaction. The process used to characterise Compounds A and B is shown in FIG. 5.

Compound A (100 µg) was dissolved in ice cold dry pyridine (20 µl, Fluka) in a siliconized glass tube, and 2-dimethylaminopyridine (DMAP, Aldrich-1 µl from a 1% solution in dry pyridine) was added and the reagents were mixed, followed quickly by the addition of Mosher acid chloride (1 µl of R(−)-α-methoxy-α-trifluoromethyl phenylacetic acid chloride or S(+)-α-methoxy-α-trifluoromethyl phenylacetic acid chloride (Fluka)) with rapid mixing. The mixture was placed on ice for about 1 min with occasional mixing, after which time ice cold ethyl acetate (200 µl) and water (50 µl) were added with rapid mixing. The sample was centrifuged for about 10 sec in an Eppendorf centrifuge, to separate the two layers, and the ethyl acetate layer was transferred to another siliconized glass tube. The procedure was repeated with another 100 µl ethyl acetate and the combined ethyl acetate layers were taken to dryness with nitrogen gas in a well ventilated fume hood. The residue was dissolved in hexanes and purified from reagents by HPLC (uPorasil, Waters, isocratic conditions: 0.7% isopropanol in hexanes, 1 ml/min). The compound of interest eluted at 1.9 min. The purity of the compound was checked by re-analysis on HPLC using 0.2% isopropanol in hexanes where the compound eluted at 5.4 min. The purified, Mosher-derivatized Compound A was stored in ethyl acetate at −20° C.

Short reaction times (1 minute) at ice temperature and rapid extraction had to be developed to reduce decomposition of the compound, whereas routine methodologies indicate reaction times of several hours to days (Queiroz et al., (2003); Alali et al., (1997)) for the reaction to go to completion. Although the parent hepoxilin methyl esters were stable and were easily derivatized in the alkaline conditions into the Mosher esters, the Mosher ester of compound A was difficult to make due to the unexpected decomposition. In addition, although the natural hepoxilin Mosher esters were well separated into enantiomers by chiral HPLC, the Mosher ester derivatives of the cyclopropyl enantiomers, compounds A and B, (also C and D, see below) were not separated by either TLC, chiral HPLC or straight phase HPLC and provided considerable difficulty for the characterisation of their structures. It was unexpected to find that TLC analysis of the Mosher ester derivatives of the cyclopropyl compounds A-D showed multiple spots when the reaction mixture or the HPLC purified compounds were spotted on TLC from a benzene or chloroform solvent, but gave a single spot when the samples were spotted from a solution of ethyl acetate or acetonitrile. This was not observed with the Mosher esters of the natural hepoxilins or the underivatized cyclopropyl racemates which were routinely stored in benzene. The purity of the Mosher derivative of compound A was verified by HPLC (0.2% isopropanol in hexanes, uPorasil column) and TLC (hexanes/isopropanol 2/1).

The absolute configuration of the C10 carbinolic center of Compound A was determined by NMR of the Mosher ester. NMR analysis (d3-acetonitrile solvent, 500 MHz) of the Mosher ester of Compound A derivatized with both S(+) and R(−) Mosher acid chlorides showed a change in the signal for the $H^{11}$ $H^{12}$ cyclopropyl protons upfield from 0.510 to 0.462 Hz (overlapping triplets-centre) and 0.416 to 0.366 Hz (overlapping triplets-centre) only in the compound derivatized with R(−) Mosher acid chloride, (i.e. S Mosher ester derivative). At the same time, the signals for the double bond protons at $H^8H^9$ were shifted downfield 5.65 to 5.7 Hz (2 triplets-centre) and 5.5 to 5.6 Hz (overlapping triplet-centre). From these diagnostic resonances of the groups proximal to the carbinolic centre, the absolute configuration was determined. Hence the difference in the chemical shift, δS-δR, for the former group is negative and for the latter group is positive. According to Queiroz et al. (2003), the group giving a negative chemical shift is placed on the left of a configurational correlation model, while the positive chemical shift group is placed on the right. Once the model is rearranged to have the carbinolic hydrogen in the back, the absolute configuration of Compound A, using the Cahn Ingold Prelog priority rules, is 10R, identifying Compound A as 10R-hydroxy-11S,12S-cyclopropyl-eicosa-5Z,8Z,14Z-trienoic acid methyl ester. The free acid can be generated from the methyl ester by conventional means, for example by alkaline hydrolysis. The optical rotation of Compound A was $[\alpha]_D$−17.6° (CHCl$_3$, 27.1° C., 589 nm).

Example 2

Separation of 10S-hydroxy-11R,12R-cyclopropyl-eicosa-5Z,8Z,14Z-trienoic acid methyl ester (anti) (Compound B) from racemic PBT-3

This example describes the isolation of 10S-hydroxy-11R, 12R-cyclopropyl-eicosa-5Z,8Z,14Z-trienoate methyl ester from racemic PBT-3. Compound B was well resolved from compound A on the Chiralcel-OD HPLC column by the method described in Example 1. The elution time of compound B was 20.4 min with hexanes-isopropanol and 15.9 min with hexanes-n-butanol. Its absolute configuration was derived from the knowledge that it belonged to the "anti" series and was the mirror image of Compound A, therefore having the structure 10S-hydroxy-11R,12R-cyclopropyl-eicosa-5Z,8Z,14Z-trienoic methyl ester. The optical rotation of Compound B was $[\alpha]_D$+16.1 (CHCl$_3$, 27.1° C., 589 nm). The free acid can be obtained by conventional methods, for example by alkaline hydrolysis of the methyl ester.

Example 3

Separation of 10R-hydroxy-11R,12R-cyclopropyl-eicosa-5Z,8Z,14Ztrienoic acid methyl ester (syn) (Compound C) from racemic PBT-4

The cyclopropyl group of compound C is syn relative to the C10 hydroxyl group.

Racemic PBT-4 was separated into its two enantiomers, compounds C and D (FIG. 2), by chiral phase HPLC, essentially as described in Example 1. Using hexanes/isopropanol about 99:1, Compound C eluted at 14.4 min, and its mirror image, compound D, at 15.5 min. Using hexanes/n-butanol about 99.2:0.8, Compound C eluted at 15.1 min, and its mirror image, compound D, at 17.4 min.

Figure 6:
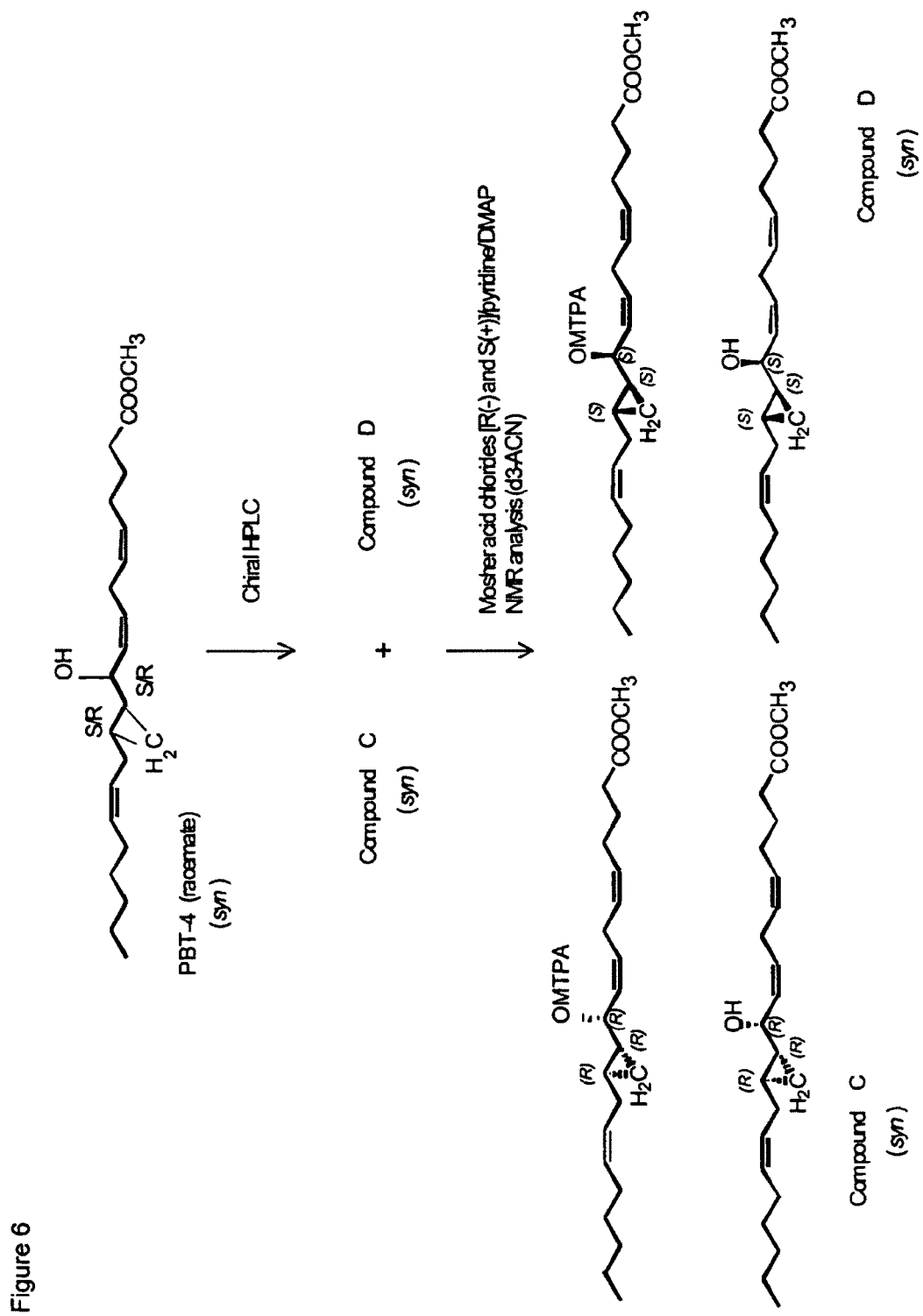
FIG. 6 shows a process used to characterise Compounds C and D.

The absolute configuration of Compound C was established by NMR of diagnostic resonances after esterification of the compound with commercial Mosher reagent (acid chloride, R(−) and S(+)), as described in Example 1. The characterisation process is shown in FIG. 6. Compound C was unstable to the alkaline conditions of the reaction (pyridine solvent with DMAP catalyst) and therefore a rapid (1 minute) reaction time at ice temperature had to be used. The Mosher esterified compound was stable in ethyl acetate or acetonitrile as judged by TLC, but not in benzene or chloroform although the purified enantiomer (not Mosher esterified) was stable in benzene or chloroform. The Mosher derivative was purified as described in Example 1 (straight phase HPLC) and purity was monitored by HPLC and TLC. The absolute configuration of the 10-hydroxyl group in Compound C was established by NMR (d3 acetonitrile solvent). As described in Example 1, the proton signals at $H^{11}H^{12}$ were shifted upfield only in the compound derivatized with R(−) Mosher acid chloride (equivalent to S ester), while the proton signals for the double bond at $H^{8,9}$ were shifted downfield in the same derivative indicating that Compound C has a 10-R-hydroxy configuration and that the absolute configuration of the compound is 10R-hydroxy-11R,12R-cyclopropyl-eicosa-5Z,8Z,14Z-trienoic acid methyl ester.

The optical rotation of Compound C was $[\alpha]_D$−99° ($CHCl_3$, 25.7° C., 589 nm). The free acid can be generated from the methyl ester by conventional means.

Example 4

Separation of 10S-hydroxy-11S,12S-cyclopropyl-eicosa-5Z,8Z,14Z-trienoic acid methyl ester (syn) (Compound D) from racemic PBT-4

Compound D was separated from compound C as described in Example 3. Its elution time was 15.5 min with hexanes/isopropanol and 17.4 min with hexanes/n-butanol. Its structure was determined from the knowledge that the relative configuration of the hydroxyl group and the cyclopropyl groups was 'syn' and that it was the mirror image of Compound C. The structure of Compound D is therefore 10S-hydroxy-11S,12S-cyclopropyl-eicosa-5Z,8Z,14Z-trienoic methyl ester. The optical rotation of Compound D was $[\alpha]_D$+82° ($CHCl_3$, 25.7° C., 589 nm). The free acid can be generated from the methyl ester by conventional means.

Example 5

Inhibition of platelet aggregation by Compounds A, B, C and D

Washed human platelets were prepared as previously described (Pace-Asciak et al., 2002). The aggregation of platelets was carried out in a conventional 4-well aggregometer with stirring of the suspension maintained at 37° C. The platelet suspension was caused to aggregate with a thromboxane stable analog, I-BOP. The isolated enantiomer compounds and their respective racemates, PBT-3 and PBT-4, were added at various concentrations to cuvettes containing 375×106 platelets/ml, 1 min prior to the addition of 5 ng I-BOP (Cayman Chemicals, Ann Arbor, Mich.). Aggregation was monitored for an additional 5 min. The results are shown in Table 1.

Compound A was nearly four times as active as compound B in inhibiting human platelet aggregation evoked in vitro in washed platelets by I-BOP, a thromboxane A2 receptor agonist. The platelet aggregation inhibitory activity of compound A was 2-fold more potent than that of the racemic PBT-3.

A less effective enantioselectivity was observed between Compounds C and D, as compared to the results obtained with Compounds A and B. Compound C seems to be more potent an inhibitor than Compound D under the conditions used.

Example 6

Antiproliferative effects of Compounds A, B, C and D on human leukemic K562 cells The human leukemic K562 cell line was established as previously reported (Qiao et al., 2003). Cells were maintained as suspension cultures in RPMI 1640 medium supplemented with 100 1.1/ml penicillin G, 100 µg/ml streptomycin, 10% (v/v) bovine serum albumin in a humidified atmosphere of 5% $CO_2$ at 37° C. Cell viability was assessed by the exclusion of Trypan blue. Incorporation of $^3$H-methyl thymidine into cell DNA was used as an assay for cell proliferation. Cells (0.5×6/well) were starved for 12 h, and were subsequently treated with the test compounds. Compounds A, B, C and D were made up at various concentrations in DMSO (0.25 to 2.5 pg/$_i$llfor A, B, C and D. Concentrations were doubled for racemates PBT-3 and PBT-4) and 1 of these solutions was added/ml volume of cells. Cells were suspended in RPMI 1640 medium. At 6 h post-treatment at 37° C. the cells were fixed and denatured essentially as described in Qiao et al. (2003), harvested and passed through Whatman GF/C glass filters. The filters were washed and counted for radioactivity.

As shown in Table 2, Compound A was about two-fold more active than Compound B in inhibiting the incorporation of $^3$H-methyl thymidine in K562 cells in vitro and the activity of Compound A was greater than that of the racemate PBT-3. The enantioselectivity between Compounds C and D was less than that between Compounds A and B.

Example 6a

Effect of Compounds A, B, C and D on Caspase-3 Cleavage

Cell culture: Human leukemia K562 cells, obtained from ATCC (American Type Culture Collection), were maintained in RPMI 1640 medium containing 100 units/ml penicillin G, 100 µg/ml streptomycin, 10% (v/v) fetal calf serum in a humidified atmosphere with 5% $CO_2$ at 37° C. The ability of the cells to exclude trypan Blue dye was used to assess cell viability.

Cell treatment: K562 cells were stored in 0.5% FBS for 15 min before the experiment. The cells, 6×10$^5$, were treated with DMSO as vehicle, or with PBT-3, PBT-4, or compounds A, B, C and D at 10 uM/dish (8 ml). Gleevec™ (STI) was used at 5 µM/dish. All experiments were without FBS and treatment lasted 6 h at 37° C. Treatment was terminated by washing the cells with ice-cold PBS buffer by centrifugation at 500×g for 5 min. Cells were lysed in buffer containing 20 mM Tris-HCl buffer, pH 7.4, 150 NaCl, 1 mM EDTA, 1 mM EGTA, 1% Triton X-100 2.5 mM sodium pyrophosphate, 1 mM beta-glycerophosphate, 1 mM sodium orthovanadate, 1 mM PMSF and 1 µM leupeptin/1 µM Aprotinin/1 µM pepstain A, on ice for 30 min. The lysates were clarified by centrifugation at 15,000×g for 15 min at 4° C. Lysates were subjected to protein assay (BCA, Pierce) and kept at −80° C.

Western blot: Thirty micrograms of protein from each sample were taken, and SDS-PAGE sample loading buffer was added. The mixture was boiled for 5 min. After centrifugation, the samples were loaded onto 15% SDS-PAGE gel and the gel was run (BioRad Protein II) for 2-3 h at 20 mA. The protein was transferred to a Trans-blot Nitrocellulose membrane (Millipore). Protein bands on the membranes were checked visually with Ponceau S-staining to ensure equivalent protein load/transfer comparing different samples. Membranes were blocked with 5% non-fat dry milk in PBS containing 0.5% Tween-20 for 1 h at room temperature, and then incubated with 1:1000 dilution of anti-caspase-3 antibody (BD Transduction Laboratories, Mississauga, Canada) overnight at 4° C. Secondary antibody of horseradish peroxidase anti-mouse antibody was used at 1:2000 dilution. Bound antibodies were detected by using enhanced chemilluminescence (ECL kit, Amersham Pharmacia Biotech) and the membranes were exposed to Hyper film for ECL detection. The same membrane was stripped by placing in buffer containing 62.5 mM Tris-HCl, pH 6.8/2% SDS/100 mM beta-mercaptoethanol at 50° C. for 30 min. The membrane was washed 3 times with PBS containing 0.5% Tween-20. The membrane was blocked by PBS buffer containing 0.5% Tween-20 and 5% skim milk. The anti-tubulin antibody (Santa Cruz, Calif.) was diluted 1:1000 and membrane analyzed by ECL as described above.

Figure 7:
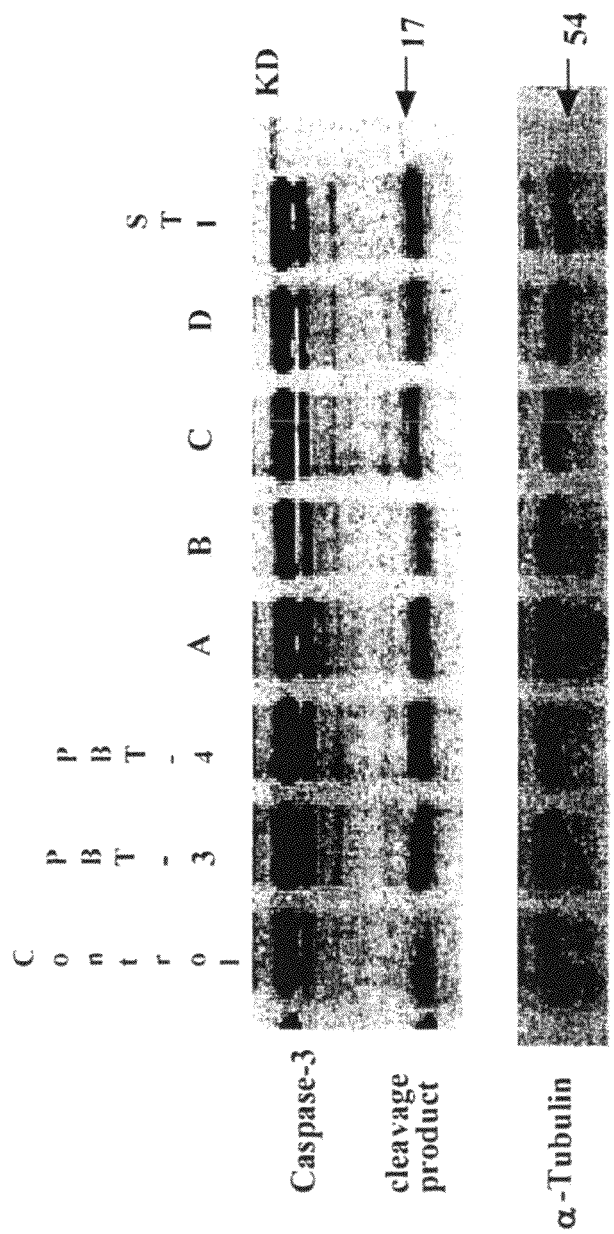
FIG. 7 shows a Western blot of Caspase-3 cleavage in the presence of the indicated compounds.

As shown in FIG. 7, PBT-3, PBT-4 and Compounds A, B, C and D all increased cleavage of caspase-3. Compound A was more active than Compound B in inducing cleavage of caspase-3 in K562 cells in vitro. The enantioselectivity between Compounds C and D was less than that between Compounds A and B.

Example 7

Separation of 8R-hydroxy-11S,12S-cyclopropyl-eicosa-5Z,9E,14Z-trienoic acid methyl ester (anti) (Compound E) from racemic PBT-1

This example describes the isolation of 8R-hydroxy-11S, 12S-cyclopropyl-eicosa-5Z,9E,14Z-trienoic acid methyl ester from racemic PBT-1. Resolution of the racemate by chiral HPLC into its two enantiomers was obtained under the conditions described for Compounds A/B or C/D with modification of the solvent system to contain only 0.2% isopropanol in hexanes. This brought about a baseline separation (peak to peak separation of nearly 7 min), with an elution time of 70-80 min. By comparison with the elution pattern of authentic chirally pure hepoxilins having an epoxide group at C11,C12 (Demin et al. (1995)), the first eluting compound, compound E (FIG. 3), was 8R-hydroxy-11S,12S-cyclopropyl-eicosa-5Z,9E,14Z-trienoic acid methyl ester.

Using hexanes/n-butanol about 99.2:0.8 and a flow rate of 1.5 ml/min, Compound E eluted at 14.6 min, and its mirror image, compound F, at 15.4 min.

The free acid can be generated from the methyl ester by conventional means.

Example 8

Separation of 8S-hydroxy-11R,12R-cyclopropyl-eicosa-5Z,9E,14Z-trienoic acid methyl ester (anti) (Compound F) from racemic PBT-1

Compound F (FIG. 3) was separated from compound E as described in Example 7. It eluted at around 80 min on chiral HPLC with hexanes/isopropanol and at 15.4 min with hexanes/n-butanol. By comparison with the structure of compound E, and knowing that it is 'anti, its structure is 8S-hydroxy-11R,12R-cyclopropyl-eicosa5Z,9E,14Z-trienoic methyl ester. The free acid can be generated from the methyl ester by conventional means.

Example 9

Separation of 8R-hydroxy-11R,12R-cyclopropyl-eicosa-5Z,9E,14Z-trienoic acid methyl ester (syn) (Compound G) from racemic PBT-2

This example describes the isolation of 8R-hydroxy-11R, 12R-cyclopropyl-eicosa-5Z,9E,14Z-trienoic acid methyl ester from racemic PBT-2. Resolution of the racemate by chiral HPLC into its two enantiomers was obtained under the conditions described for Compounds A/B or C/D with modification of the solvent system to contain only 0.8% n-butanol in hexanes and using a flow rate of 1.5 ml/min, Compound G eluted at 15.2 min, and its mirror image, compound H, at 16.7 min. By comparison with the elution pattern of authentic chirally pure hepoxilins having an epoxide group at C11,C12 (Demin et al. (1995)), the first eluting compound, compound G (FIG. 4), was 8R-hydroxy-11R,12R-cyclopropyl-eicosa-5Z,9E,14Z-trienoic acid methyl ester.

The free acid can be generated from the methyl ester by conventional means.

Example 10

Separation of 8S-hydroxy-11S,12S-cyclopropyl-eicosa-5Z,9E,14Z-trienoic acid methyl ester (syn) (Compound H) from racemic PBT-2

Compound H (FIG. 4) was separated from compound G as described in Example 9. It eluted at 16.7 min with hexanes/n-butanol. By comparison with the structure of compound G, and knowing that it is 'syn', its structure is 8S-hydroxy-11S,12S-cyclopropyl-eicosa5Z,9E,14Z-trienoic methyl ester. The free acid can be generated from the methyl ester by conventional means.

Example 11

PPAR Gamma Transactivation Activity

Cell Culture, Plasmids and Transfections

This is an example of a transactivation assay for determining PPAR gamma modulating activity and demonstrates that the racemates PBT1, -2, -3 and -4 are PPAR gamma agonists.

Gal4-PPAR gammaLBD (Helledie et al., 2000), UASx4-TK luc (Chen and Evans, 1995) and CMV-beta-galactosidase (available commercially, e.g. Clontech) were used in these assays to show PPAR gamma transactivation. The UASx4-TK-luc reporter construct (where UAS refers to "upstream activator sequence") contains four Gal4-responsive elements. The plasmid Gal4-PPAR gammaLBD encodes a Gal4-DBD-PPAR gamma-LBD fusion protein (i.e. the DNA-binding domain, DBD, of Gal4 fused to the ligand-binding domain, LBD, of PPAR gamma) capable of transactivating the UASx4-TK-luc reporter plasmid by binding to the UAS. The CMV-beta-galactosidase plasmid (where CMV is cytomegalovirus) was used for normalization of experimental values.

Mouse embryonic fibroblasts (MEFs) were grown in AmnioMax basal medium (Gibco) supplemented with 7.5% Amniomax supplement C-100 (Gibco), 7.5% Fetal Bovine Serum (FBS), 2 mM Glutamine, 62.5 microg/ml penicillin and 100 microg/ml Streptomycin (growth medium). Alternatively, ME3 cells were grown in DMEM supplemented with 10% Calf Serum (CS), 62.5 microg/ml penicillin and 100 microg/ml Streptomycin (growth medium). The cells were replated, typically in 24 well plates, so that at the time of transfection the cells were 50-70% confluent.

The cells were transfected with Gal4-PPAR gammaLBD (Helledie et al 2000), UASx4-TK luc (Chen and Evans, 1995) and CMV-beta-galactosidase (available commercially, e.g. Clontech) using Lipofectamin Plus (Invitrogen) or Metafectane (Biontex) according to the manufacturer's instructions. Briefly, per well in a 24 well plate, UASx4TKluc (0.2 microg) Gal4-PPAR gammaLBD (or pM-hPPAR gamma-LBD; 0.1 microg) and CMV-beta-galactosidase (0.05 microg) in 30 μL DMEM (free of serum and antibiotics) was mixed with 30 microL DMEM (free of serum and antibiotics) containing 1 microL metafectenein. The mixture was incubated at room temperature for 20 min to allow formation of nucleic acid-lipid complexes and then approximately 60 micros was added to each well containing the 50-70% confluent cells. The cells were incubated at 37° C. in a $CO_2$ incubator for 6 to 12 hours and the medium was then replaced with medium supplemented with antibiotics and the ligand of interest (e.g., hepoxilin A3 (Biomol), hepoxilin B3 (Biomol), compounds referred to in Table 6 or rosiglitazone (Avandia) as a positive control, all dissolved in DMSO) or a comparable volume of DMSO (<0.5% of total cell culture volume). Cells were harvested after 12-24 hours and luciferase and beta-galactosidase activities were measured according to standard protocols.

PPAR transactivation was over 5-fold higher with rosiglitazone (a known PPAR gamma agonist) than with DMSO alone, and each of 10 microM PBT-1, -2, -3 or -4 resulted in 18 to 27% of the transactivation achieved with rosiglitazone (see Table 3), thus demonstrating that these compounds are PPAR gamma agonists. The respective free carboxylic acids of the racemates, PBT01, PBTO2 and PBT03, were also active (Table 3).

Example 12

PPAR Gamma Transactivation Activity of Enantiomers

This is an example of a transactivation assay for determining PPAR gamma modulating activity and demonstrates that the racemates PBT1, -2, -3 and -4, and their enantiomers are PPAR gamma agonists. The assays were carried out essentially as described above in Example 9 but using the enantiomers (Compounds A-F) as described and prepared above.

The results are shown below in Table 4. Each experiment was carried out with triplicate samples with 0.1, 1 or 10 microM racemate or purified enantiomer. The results of three separate experiments are shown in Tables 4a, 4b and 4c respectively.

To summarize, all enantiomers exhibit PPAR gamma transactivation activity (as would be expected also for PBT-2 in light of these data).

Compound F is clearly able to induce higher fold PPAR gamma transactivation than compound E or the PBT-1 racemic mixture. Thus, compound F is particularly useful for the modulation of PPAR, in particular for the treatment of PPAR gamma mediated conditions.

There is no apparent difference in PPAR gamma activation by the PBT-3 racemic mixture and the individual enantiomers (Compounds A and B). However, in silico modelling of the PBT enantiomers demonstrated a preferential binding of 10S-hydroxy-11R,12R-cyclopropyl-eicosa5Z,8Z,14Z-trienoic acid (Compound B in Example 2) to PPAR gamma than 10R-hydroxy-11S,12Scyclopropyl-eicosa-5Z,8Z,14Z-trienoic acid (Compound A in Example 1). As a result, compound B might have other properties (such as beneficial co-factor recruitment), which would make it particularly useful for the modulation of PPAR, in particular for the treatment of PPAR gamma mediated conditions.

Compound D appears to induce higher fold PPAR gamma transactivation than compound C, but exhibits no significant difference in PPAR gamma activation relative to the PBT-4 racemic mixture. Thus, compound D would particularly useful for the modulation of PPAR, in particular for the treatment of PPAR gamma mediated conditions.

TABLE 1

INHIBITORY EFFECTS OF COMPOUNDS A, B, C, D ON I-BOP EVOKED HUMAN PLATELET AGGREGATION IN VITRO WITH WASHED PLATELETS

| Compound* | $IC_{50}$ (nM) |
| --- | --- |
| PBT-3 (racemate) | 54 ± 9 |
| A | 27 ± 7 |
| B | 101 ± 27 |
| PBT-4 (racemate) | 79 ± 17 |
| C | 60 ± 12 |
| D | 82 ± 18 |

*Compounds are methyl esters.

TABLE 2

INHIBITION OF $^3$H-METHYL THYMIDINE INCORPORATION IN K562 CELLS IN VITRO

| Compound* | $IC_{50}$ (μM) |
| --- | --- |
| PBT-3 (racemate) | 4.6 |
| A | 3.6 |
| B | 7.6 |
| PBT-4 (racemate) | 4.9 |
| C | 4.0 |
| D | 5.2 |

*Compounds are methyl esters.

TABLE 3

PPAR GAMMA TRANSACTIVATION

| Racemate (10 microM) | PPAR Activation as % of positive control (Avandia) | Vehicle Activation as % of positive control (Avandia) |
| --- | --- | --- |
| PBT-1 (me ester) | 21 +/− 2 | 2.4 +/− 0.7 |
| PBT-2 (me ester) | 27 +/− 5 | 2.4 +/− 0.7 |
| PBT-3 (me ester) | 18 +/− 1 | 1.6 +/− 0.4 |
| PBT-4 (me ester) | 19 +/− 1 | 1.6 +/− 0.4 |
| PBT-01 (free acid) | 16 +/− 4 | 1.5 +/− 0.4 |
| PBT-02 (free acid) | 17 +/− 2 | 1.5 +/− 0.4 |
| PBT-03 (free acid) | 14 +/− 4 | 1.4 +/− 0.3 |

TABLE 4

ENANTIOMER PPAR GAMMA TRANSACTIVATION
Table 4a: Experiment 1

| Compound | PPAR Activation as % of positive control (Avandia) | | |
| --- | --- | --- | --- |
| | 0.1 microM | 1 micro M | 10 microM |
| PBT-1 (me ester) racemate | 17 +/− 2 | 57 +/− 6 | ND |
| Compound E | 5 +/− 1 | 11 +/− 1 | 55 +/− 8 |
| Compound F | 7 +/− 1 | 12 +/− 7 | 92 +/− 7 |
| PBT-3 (me ester) racemate | 11 +/− 2 | 15 +/− 2 | 42 +/− 8 |
| Compound A | 11 +/− 4 | 14 +/− 4 | 63 +/− 34 |
| Compound B | 11 +/− 3 | 21 +/− 3 | 44 +/− 11 |
| PBT-4 (me ester) racemate | 13 +/− 2 | 13 +/− 3 | 60 +/− 9 |
| Compound C | 14 +/− 4 | 16 +/− 3 | 38 +/− 8 |
| Compound D | 14 +/− 3 | 17 +/− 3 | 69 +/− 15 |

TABLE 4b

Experiment 2

| Compound | PPAR Activation as % of positive control (Avandia) | | |
|---|---|---|---|
| | 0.1 microM | 1 micro M | 10 microM |
| PBT-1 (me ester) racemate | 7 +/− 1 | 35 +/− 5 | ND |
| Compound E | 4 +/− 1 | 4 +/− 1 | 14 +/− 2 |
| Compound F | 5 +/− 1 | 5 +/− 5 | 69 +/− 12 |
| PBT-3 (me ester) racemate | 4 +/− 1 | 8 +/− 1 | 41 +/− 5 |
| Compound A | 4 +/− 1 | 11 +/− 1 | 34 +/− 1 |
| Compound B | 4 +/− 1 | 10 +/− 1 | 35 +/− 11 |
| PBT-4 (me ester) racemate | 4 +/− 1 | 7 +/− 1 | 32 +/− 1 |
| Compound C | 4 +/− 1 | 6 +/− 1 | 14 +/− 1 |
| Compound D | 4 +/− 1 | 5 +/− 1 | 18 +/− 1 |

TABLE 4c

Experiment 3

| Compound | PPAR Activation as % of positive control (Avandia) | | |
|---|---|---|---|
| | 0.1 microM | 1 micro M | 10 microM |
| PBT-1 (me ester) racemate | 6 +/− 2 | 34 +/− 2 | 58 +/− 12 |
| Compound E | 7 +/− 3 | 11 +/− 2 | 27 +/− 7 |
| Compound F | 8 +/− 2 | 18 +/− 5 | 78 +/− 34 |
| PBT-3 (me ester) racemate | 8 +/− 2 | 18 +/− 4 | 32 +/− 4 |
| Compound A | 8 +/− 2 | 12 +/− 1 | 27 +/− 5 |
| Compound B | 10 +/− 3 | 16 +/− 6 | 30 +/− 10 |
| PBT-4 (me ester) racemate | 7 +/− 1 | 15 +/− 7 | 33 +/− 8 |
| Compound C | 9 +/− 3 | 7 +/− 1 | 17 +/− 3 |
| Compound D | 7 +/− 2 | 8 +/− 1 | 33 +/− 7 |

REFERENCES

1. Alali, F. Q., Y. Zhang, et al. (1997). "(2,4-cis and trans)-Gigantecinone and 4-deoxygigantecin, bioactive nonadjacent bis-tetrahydrofuran annonaceous acetogenins, from goniothalamus giganteus," J. Nat. Prod. 60: 929-933.
2. Chawla, A., and Lazar, M. A. (1994) Proc. Natl. Acad. Sci. U.S.A. 91, 1786-1790.
3. Chen and Evans, (1995), Nature 377, 454-457.
4. Demin, P., D. Reynaud, et al. (1995). "High-performance liquid chromatographic separation of fluorescent esters of hepoxilin enantiomers on a chiral stationary phase," J. Chromatogr. 672: 282-289.
5. Helledie et al. (2000). J. Lipid Res. 41, 1740-1751.
6. Jankov, R. P., X. Luo, et al. (2002). "Hepoxilin analogs inhibit bleomycin-induced pulmonary fibrosis in the mouse." J. Pharm. Exp. Ther. 301: 435-440.
7. Kliewer, S. A., Lenhard, J. M., Wilson, T. M., Patel, I., Morris, D. C. and Lehman, J. M. (1995) Cell 83 813-819.
8. Kopelovich et al., (2002), Molecular Cancer Therapeutics, 1, 347-355.
9. Lehmann et al., (1995), J. Biol. Chem. 270, 12953-12956.
10. Li, X., N. Qiao, et al. (2005). "The hepoxilin analog, PBT-3, inhibits growth of K-562 CML solid tumours in vivo in nude mice." In Vivo 19: 185-190.
11. Pace-Asciak, C. R., D. Reynaud, et al. (2002). "A new family of thromboxane receptor antagonists with secondary thromboxane synthase inhibition." J. Pharmacol. Exper. Ther. 301: 618-624.
12. Pace-Asciak, C. R., X. Li, et al. (2006). "Hepoxilin analogs, potential new therapeutics in disease." Current Pharmaceutical Design 12: 963-969.
13. Qiao, N., J. Lam, et al. (2003). "The hepoxilin analog PBT-3 induces apoptosis in BCR-ABL-positive K562 leukemia cells." Anticancer Res. 23: 30 3617-3622.
14. Queiroz, E. F., J.-L. Wolfender, et al. (2003). "Determination of the absolute configuration of 6-alkylated a-pyrones from ravensara crassifolia by LC-NMR." Phytochem. Anal. 14: 34-39.
15. Rumi et al., (2004), Curr. Med. Chem. Anti-Canc. Agents, 4, 465-477.
16. Spiegelman, B. M. Diabetes 47, 507-514, 1998.
17. Tan et al., (2003), Am. J. Clin. Dermatol., 4, 523-530.
18. Tontonoz, P., Hu, E., Graves, R. A., Budavari, A. I., and Spiegelman, B. M. (1994) Genes & Dev. 8, 1224-1234.

What is claimed is:

1. A compound of formula:

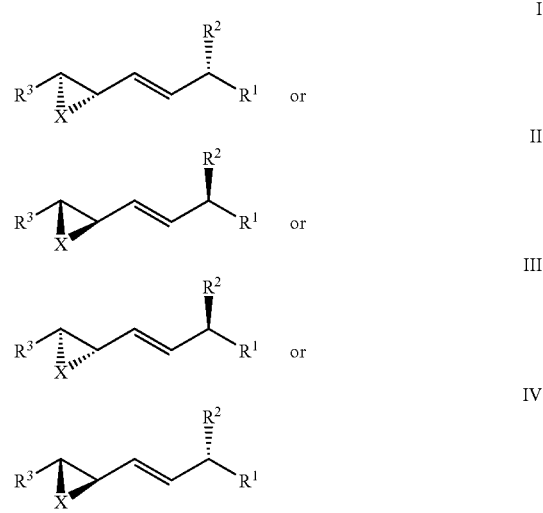

wherein,

X is $CH_2$;

$R^1$ is lower alkyl, alkenyl or alkynyl; lower alcohol, saturated or unsaturated; aryl; substituted aryl; —$(CH_2)_n$-phenyl where n is 1 to 9; or Z-$R^5$, wherein Z is a single bond or a C1-C10 carbon chain optionally substituted with —OH and/or halogen and/or optionally containing up to three double or triple bonds or a mixture of double and triple bonds up to a maximum of three; and $R^5$ is C1-C10 alkyl OH, C1-C10 alkyl-halide, C1-C10 alkyl N3, C1-C10 alkyl-NH2 or $COOR^6$ or $CONHR^6$, wherein $R^6$ is H, C5 or C6 cycloalkyl, C5-C6 aryl, a sugar moiety or C1-C10 alkyl or alkenyl optionally substituted with COOH, C5-C6 aryl, heterocycle or a sugar moiety;

$R^2$ OH, halogen, $NH_2$, SH, $OPO_3H$, lower alkyl, alkenyl or alkynyl, lower alcohol, O-lower alkyl or alkenyl, S-lower alkyl or alkenyl, NH-lower alkyl or alkenyl, or N his-lower alkyl or alkenyl; and $R^3$ is a C4-C15 carbon chain optionally substituted with —$OR^7$, wherein $R^7$ is H, lower alkyl, alkenyl or alkynyl; wherein $R^3$ optionally contains up to three double or triple bonds or a mixture of double and triple bonds up to a maximum of three;

or a pharmaceutical salt, methyl ester, sugar amide, or sugar ester thereof.

2. The compound of claim 1, wherein:

$R^1$ is COOH, lower alkyl, lower alkenyl, lower alkynyl, aryl, substituted aryl, —$(CH_2)_n$-phenyl where n is 1 to 9;

lower alkoxy, saturated or unsaturated; —CH$_2$CH=CH—(CH$_2$)$_3$—COR$^8$ wherein R$^8$ is OH, O-lower alkyl or alkenyl; COOR$^6$ or CONHR$^6$, wherein R$^6$ is CH$_3$ or a sugar moiety;

R$^2$ is OH, NH$_2$, SH, OPO$_3$H, lower alkyl or alkenyl; or O-lower alkyl or alkenyl; or N-lower alkyl or alkenyl; or S-lower alkyl or alkenyl; and R$^3$ is lower alkyl, alkenyl or alkynyl; or —CH$_2$—CH=CH—(CH$_2$)$_4$—R$^9$ wherein R$^9$ is CH$_3$, CH$_2$OH, CH$_2$—O-lower alkyl or alkenyl, aryl or substituted aryl, or (CH$_2$)$_n$-phenyl where n is 1 to 9;

or a pharmaceutical salt, methyl ester, sugar amide, or sugar ester thereof.

3. A compound of formula:

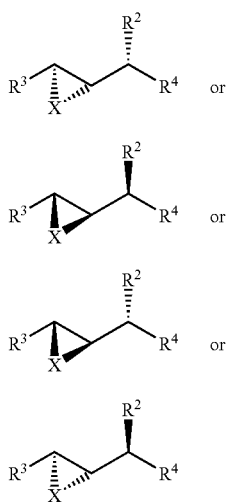

wherein X is CH$_2$;

R$^2$ is H, OH, halogen, NH$_2$, SH, OPO$_3$H, lower alkyl, alkenyl or alkynyl, lower alcohol, O-lower alkyl or alkenyl, S-lower alkyl or alkenyl, NH-lower alkyl or alkenyl, or N bis-lower alkyl or alkenyl;

R$^3$ is a C4-C15 carbon chain optionally substituted with —OR$^7$, wherein R$^7$ is —H, lower alkyl, alkenyl or alkynyl; and wherein R$^3$ optionally contains up to three double or triple bonds or a mixture of double and triple bonds up to a maximum of three; and R$^4$ is lower alkyl, alkenyl or alkynyl; lower alcohol, saturated or unsaturated; aryl; substituted aryl; —(CH$_2$)$_n$-phenyl where n is 1 to 9; or Z—R$^5$, wherein Z is a single bond or a C1-C10 carbon chain optionally substituted with —OH and/or halogen and/or optionally containing up to three double or triple bonds or a mixture of double and triple bonds up to a maximum of three; and R$^5$ is C1-C10 alkyl OH, C1-C10 alkyl-halide, C1-C10 alkyl N3, C1-C10 alkyl —NH2 or COOR$^6$ or CONHR$^6$, wherein R$^6$ is H, C5 or C6 cycloalkyl, C5-C6 aryl, a sugar moiety or C1-C10 alkyl or alkenyl optionally substituted with COOH, C5-C6 aryl, heterocycle or a sugar moiety;

or a pharmaceutical salt, methyl ester, sugar amide, or sugar ester thereof.

4. The compound of claim 3, wherein:

R$^2$ is OH, NH$_Z$, SH, OPO$_3$H, lower alkyl or alkenyl; or O-lower alkyl or alkenyl; or N-lower alkyl or alkenyl; or S-lower alkyl or alkenyl;

R$^3$ is lower alkyl, alkenyl or alkynyl; or —CH$_2$—CH=CH—(CH$_2$)$_4$—R$^9$ wherein R$^9$ is CH$_3$, CH$_2$OH, CH$_2$—O-lower alkyl or alkenyl, aryl or substituted aryl, or(CH$_2$)$_n$-phenyl where n is 1 to 9; and R$^4$ is lower alkyl, alkenyl or alkynyl; lower alkoxy, saturated or unsaturated; or —CH=CH—CH$_2$—CH=CH—(CH$_2$)$_3$—COR$^8$ wherein R$^8$ is OH, O-lower alkyl or alkenyl; COOR$^6$ or CONH R$^6$, wherein R$^6$ is CH$_3$ or a sugar moiety;

or a pharmaceutical salt, methyl ester, sugar amide, or sugar ester thereof.

5. The compound of claim 1, wherein the substituted aryl is phenyl substituted with OH, I, Br, Cl, lower alkyl and/or lower alkenyl.

6. The compound of claim 1, wherein the sugar is a monosaccharide or disaccharide.

7. The compound of claim 6, wherein the monosaccharide is selected from glucose, fructose, galactose or ribose and the disaccharide is selected from sucrose, maltose or lactose.

8. The compound of claim 2, wherein the compound is selected from:
(a) 8R-hydroxy-11S, 12S-cycopropyl-eicosa-5Z,9E, 14Z-trienoic acid;
(b) 8S-hydroxy-11R, 12R-cycopropyl-eicosa-5Z,9E, 14Z-trienoic acid;
(c) 8R-hydroxy-11R, 12R-cycopropyl-eicosa-5Z,9E, 14Z-trienoic acid;
(d) 8S-hydroxy-11S, 12S-cycopropyl-eicosa-5Z,9E, 14Z-trienoic acid; or
(e) a pharmaceutical salt thereof, a methyl ester, sugar amide or sugar ester of any of compounds (a) to (d).

9. The compound of claim 4, wherein the compound is selected from;
(a) 10R-hydroxy-11S, 12S-cycopropyl-eicosa-5Z,8E, 14Z-trienoic acid;
(b) 10R-hydroxy-11R, 12R-cycopropyl-eicosa-5Z,8E, 14Z-trienoic acid;
(c) 10R-hydroxy-11R, 12R-cycopropyl-eicosa-5Z,8E, 14Z-trienoic acid;
(d) 10R-hydroxy-11S, 12S-cycopropyl-eicosa-5Z,8E, 14Z-trienoic acid; or
(e) a pharmaceutical salt thereof, a methyl ester, sugar amide or sugar ester of any of compounds (a) to (d).

10. The compound of claim 9, wherein the compound is selected from 10R-hydroxy-11S, 12S-cyclopropyl-eicosa-5Z,8Z,14Z-trienoic acid or 10S-hydroxy-11R,12R-cyclopropyl-eicosa-5Z,8Z,14Z-trienoic acid or a methyl ester thereof.

11. The compound of claim 9, wherein the compound is selected from 10R(−)-hydroxy-11S, 12S-cyclopropyl-eicosa-5Z,8Z,14Z-trienoic acid or 10S(+)-hydroxy-11R, 12R-cyclopropyl-eicosa-5Z,8Z,14Z-trienoic acid or a methyl ester thereof.

12. The compound of claim 9, wherein the compound is selected from 10R-hydroxy-11R, 12R-cyclopropyl-eicosa-5Z,8Z,14Z-trienoic acid or 10S-hydroxy-11S,12S-cyclopropyl-eicosa-5Z,Z,14Z-trienoic acid or a methyl ester thereof.

13. The compound of claim 9, wherein the compound is selected from 10R (−)-hydroxy-11R, 12R-cyclopropyl-eicosa-5Z,8Z,14Z-trienoic acid or 10S(+)-hydroxy-11S,12S-cyclopropyl-eicosa-5Z,8Z,14Z-trienoic acid or a methyl ester thereof.

14. The compound of claim 9, wherein the compound is selected from 10R(−)-hydroxy-11S, 12S-cyclopropyl-eicosa-5Z,8Z,14Z-trienoic acid.

15. The compound of claim 1, wherein the compound is a PPAR gamma modulator.

16. A pharmaceutical composition comprising at least one of the compounds of claim 1 and/or a pharmaceutically acceptable salt thereof.

17. The pharmaceutical composition of claim 16 further comprising a pharmaceutically acceptable carrier.

18. The pharmaceutical composition of claim 17, wherein the pharmaceutically acceptable carrier comprises one or more compatible solid or liquid delivery systems.

19. The compound of claim 3, wherein $R^5$ is $COOR^6$ or $CONHR^6$.

* * * * *